(12) United States Patent
Widholm et al.

(10) Patent No.: US 7,847,152 B2
(45) Date of Patent: *Dec. 7, 2010

(54) USE OF TRYPTOPHAN INDOLE AND ANTHRANILATE ANALOGS AS PLANT TRANSFORMATION SELECTION AGENTS

(75) Inventors: Jack M. Widholm, Tolono, IL (US); Pierluigi Barone, Champaign, IL (US); Xing-Hai Zhang, Boca Raton, FL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 597 days.

This patent is subject to a terminal disclaimer.

(21) Appl. No.: 11/770,030

(22) Filed: Jun. 28, 2007

(65) Prior Publication Data

US 2008/0028488 A1 Jan. 31, 2008

Related U.S. Application Data

(60) Provisional application No. 60/806,280, filed on Jun. 30, 2006.

(51) Int. Cl.
*A01H 5/00* (2006.01)
*A01H 1/04* (2006.01)
*C12N 15/82* (2006.01)

(52) U.S. Cl. .................. 800/278; 800/298; 435/410
(58) Field of Classification Search .................. None
See application file for complete search history.

(56) References Cited

U.S. PATENT DOCUMENTS

| 5,545,817 | A | * | 8/1996 | McBride et al. ............. 800/287 |
| 5,679,560 | A | * | 10/1997 | Ligon et al. ................. 435/183 |
| 5,939,602 | A | * | 8/1999 | Volrath et al. ............... 800/300 |
| 5,965,727 | A | * | 10/1999 | Song et al. .................. 536/24.1 |
| 6,118,047 | A | | 9/2000 | Anderson et al. |
| 6,118,947 | A | * | 9/2000 | Suh ............................. 396/90 |
| 6,271,016 | B1 | | 8/2001 | Anderson et al. |
| 6,388,174 | B1 | * | 5/2002 | Wakasa et al. .............. 800/300 |
| 6,515,201 | B2 | | 2/2003 | Anderson et al. |
| 6,563,025 | B1 | * | 5/2003 | Song et al. .................. 800/300 |

OTHER PUBLICATIONS

Widholm, Plant Physiology, 1981, vol. 67, pp. 1101-1104.*
Bernasconi et al., "Functional Expression of *Arabidopsis thaliana* Anthranilate Synthase Subunit I in *Escherichia coli*," *Plant Physiol.*, 106: 353-358 (1994).
Cho et al., "Increasing Tryptophan Synthesis in a Forage Legume *Astragalus sinicus* by Expressing the Tobacco Feedback-Insensitive Anthranilate Synthase (ASA2) Gene," *Plant Physiology*, 123: 1069-1076 (2000).
Song et al., "Tissue Culture-Specific Expression of a Naturally Occurring Tobacco Feedback-Insensitive Anthranilate Synthase," *Plant Physiol.*, 117: 533-543 (1998).
Svab et al., "High-frequency Plastid Transformation in Tobacco by Selection for a Chimeric aadA Gene," *Proc. Natl. Acad. Sci.* USA, 90: 913-917 (1993).
Svab et al., "Stable Transformation of Plastics in Higher Plants," *Proc. Natl. Acad. Sci.* USA, 87: 8526-8530 (1990).
Widholm et al., "Utilization of Indole Analogs by Carrot and Tobacco Cell Tryptophan Synthase in Vivo and in Vitro," *Proc. Natl. Acad. Sci.* USA, 67: 1101-1104 (1981).

* cited by examiner

*Primary Examiner*—Eileen B O Hara
(74) *Attorney, Agent, or Firm*—Barnes & Thornburg LLP; Alice O. Martin

(57) ABSTRACT

Methods and compositions are described using tryptophan analogs, indole analogs, and mixtures thereof as agents for selecting plant cells that have been transformed with an anthranilate synthase (ASA2) gene or a fragment thereof, where the ASA2 gene encodes a feedback-insensitive form of anthranilate synthase (AS).

6 Claims, 31 Drawing Sheets pAST-IV

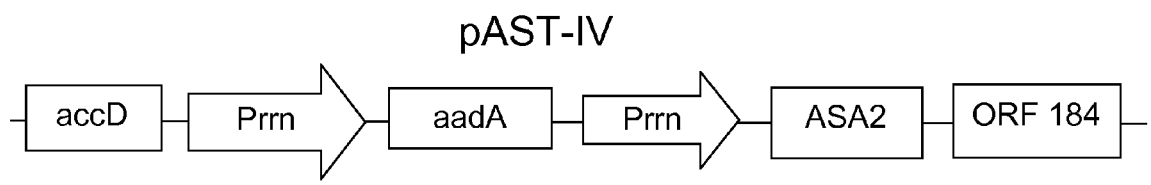

FIG. 3 pAST-IV

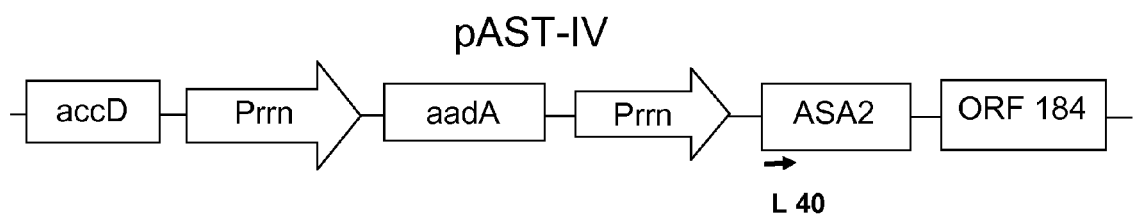

```
gaattcggcttGGCTCCAAGTTGTTCAAGAATAGTGGC
GTTGAGTTTCTCGACCCTTTGACTTAGGATTAGTCAGT
TCTATTTCTCGATGGGGCGGGGAAGGGATATAACTCAG
CGGTAGAGTGTCACCTTGACGTGGTGGAAGTCATCAGT
TCGAGCCTGATTATCCCTAAGCCCAATGTGAGTTTTC
TAGTTGGATTTGCTCCCCGCCGTCGTTAATGAGAAT
                              P1
GGATAAGAGGCTCGTGGA*TTGACG*TGAGGGGGCAGGG
       P2
ATGGC*TATATT*CTGGGAGCGAACTCCGGGCGAATATG
                             rbs
AAGCGCATGGATCTCGAGTTGTAGGGAGGGATTTATGg
     L40→                             M
cttctaaaagcgggaacttgattccgctgcacaaa---
 A   S   K   S   G   N   L   I   P   L   H   K   -
```

FIG. 4A

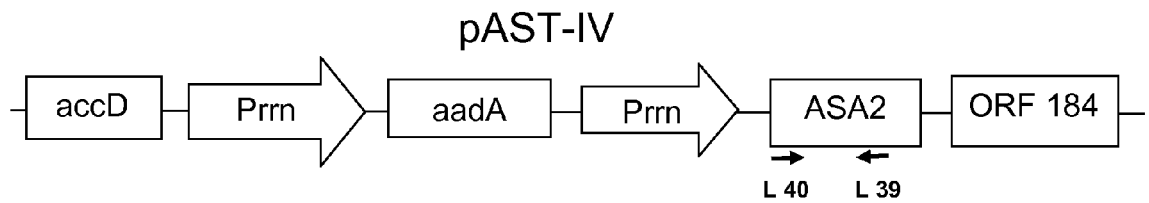

```
AACGCTTGGAAATATTAGTGTCTAGAGTACAAGGAATTGAGTCTCCAAGGTTATCTCCCG
 V  L  W  I  S  V  L  M  L  L  D  L  H  *  P  R  E  T  *  Q
GTTCTGTGGATTTCTGTACTCATGCTTTTGGACCTTCATTAACCAAGGGAAACATGACAA
 V  R  S  T  R  M  L  S  Y  K  Q  R  S  T  L  L  Q  E  T  Y
GTGAGGAGTACAAGAATGCTGTCTTACAAGCAAAGGAGCACATTGCTGCAGGAGACATAT
                                      CGACTGGGTAAACTTCACA
 F  K  S  F  *  V  N  A  L  R  E  E  H  L  L  T  H  L  K  C
TTCAAATCGTTTTAAGTCAACGCTTTGAGAGAAGAACATTTGCTGACCCATTTGAAGTGT
TGTCT 5' L39
 T  E  H  *  E  L  *  I  Q  A  H  I  *  L  T  Y  K  P  E  A
ACAGAGCATTAAGAATTGTGAATCCAAGCCCATATATGACTTACATACAAGCCAGAGGCT
```

FIG. 4B

```
                                 CTAAAAGCGGGAACTTGATTCCGC 3' L40
CTAAAAGCGGGAACTTGATTCCGCTGCACAAAACCATTTTTTCTGATCATCTGACTCCGG
TGCTGGCTTACCGGTGTTTGGTGAAAGAAGACGACCGTGAAGCTCCAAGCTTTCTCTTTG
AATCCGTTGAACCTGGTTTTCGAGGTTCTAGTGTTGGTCGCTACAGCGTGGTGGGGCTC
AACCATCTATGGAAATTGTGGCTAAGGAACACAATGTGACTATATTGGACCACCACACTG
GAAAATTGACCCAGAAGACTGTCCAAGATCCCATGACGATTCCGAGGAGTATTCTGAGG
GATGGAAGCCCAGACTCATTGATGAACTTCCTGATACCTTTTGTGGTGGATGGGTTGGTT
ATTTCTCATATGACACAGTTCGGTATGTAGAGAACAGGAAGTTGCCATTCCTAAGGGCTC
CAGAGGATGACCGGAACCTTGCAGATATTCAATTAGGACTATACGAAGATGTCATTGTGT
TTGATCATGTTGAGAAGAAAGCACATGTGATTCACTGGGTGCAGTTGGATCAGTATTCAT
CTCTTCCTGAGGCATATCTTGATGGGAAGAAACGCTTGGAAATATTAGTGTCTAGAGTAC
AAGGAATTGAGTCTCCAAGGTTATCTCCCGGTTCTGTGGATTTCTGTACTCATGCTTTTG
GACCTTCATTAACCAAGGGAAACATGACAAGTGAGGAGTACAAGAATGCTGTCTTACAAG
CAAAGGAGCACATTGCTGCAGGAGACATATTTCAAATCGTTTTAAGTCAACGCTTTGAGA
                   CGACTGGGTAAACTTCACATGTCT 5' L39
GAAGAACATTTGCTGACCCATTTGAAGTGTACAGAGCATTAAGAATTGTGAATCCAAGCC
ATATATGACTTACATACAAGCCAGAGGCTGTATTTTAGTTGCATCGAGCCCAGAAATTT
TGACACGTGTGAAGAAGAGAAGAATTGTTAATCGACCACTGGCTGGGACAAGCAGAAGAG
GGAAGACACCTGATGAGGATGTGATGTTGGAAATGCAGATGTTAAAAGATGAGAAACAAC
GCGCAGAGCACATCATGCTGGTTGATTTAGGACGAAATGATGTAGGAAAGGTGTCAAAAC
CTGGTTCTGTGAATGTCGAAAAGCTCATGAGCGTTGAGCGGTATTCCCATGTGATGCACA
TAAGCTCCACGGTCTCTGGAGAGTTGCTTGATCATTTAACCTGTTGGGATGCACTACGTG
CTGCATTGCCTGTTGGGACCGTCAGTGGAGCACCAAAGGTAAAGGCCATGGAGTTGATTG
ATCAGCTAGAAGTAGCTCGGAGAGGGCCTTACAGTGGTGGGTTTGGAGGCATTTCCTTTT
CAGGTGACATGGACATCGCACTAGCTCTAAGGACGATGGTATTCCTCAATGGAGCTCGTT
ATGACACAATGTATTCATATACAGATGCCAGCAAGCGTCAGGAATGGGTTGCTCATCTCC
AATCCGGGGCTGGAATTGTGGCTGATAGTAATCCTGATGAGGAACAGATAGAATGCGAGA
ATAAAGTAGCCGGTCTGTGCCGAGCCATTGACTTGGCCGAGTCAGCTTTTGTAAAGGGAA
GACACAAACCGTCAGTCAAGATAAATGGTTCTGTGCCAAATCTATTTTCAAGGGTACAAC
GTCAAACATCTGTTATGTCGAAGGACAGAGTACATGAGAAAAGAAACTAGCGAATATGAA
GATGTACATAAATTCTAAAGTGGTTTTCTTGTTCAGTTTAATCTTTTACTGGATTGAGAC
TGTAGTTGCTGAAGATAGTTGTTTAGAATGACCTTCATTTTGGTGTTCCTGAAAGGACAG
TGCACATATATAGCAAATTGATCAAATGTTTAATCCTTGTATGCGGGTGAGAATCAATGC
CATCAGCAATTTGG
                                                    SIZE 815 BP
```

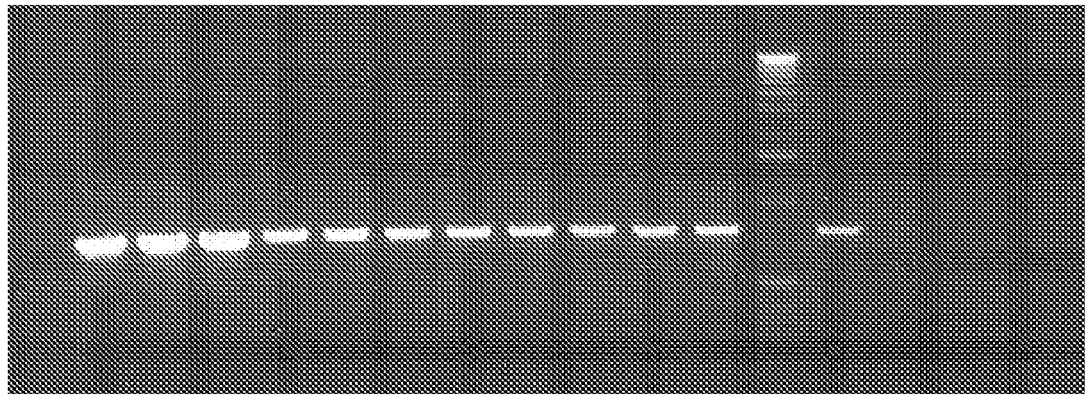

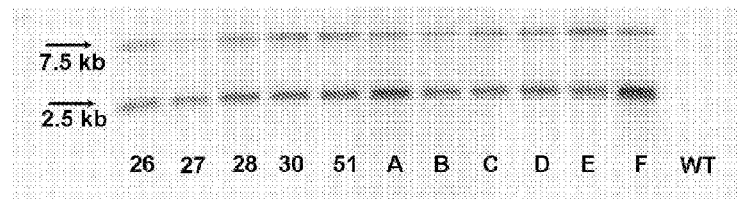
FIG. 7
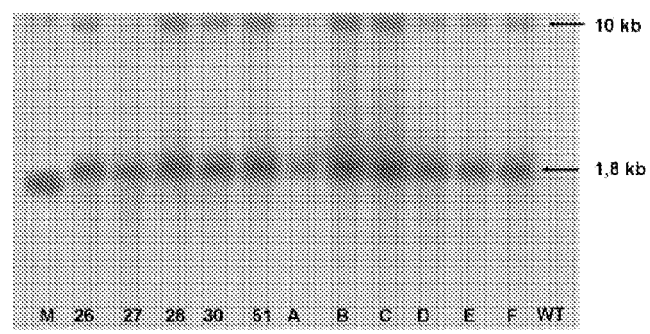
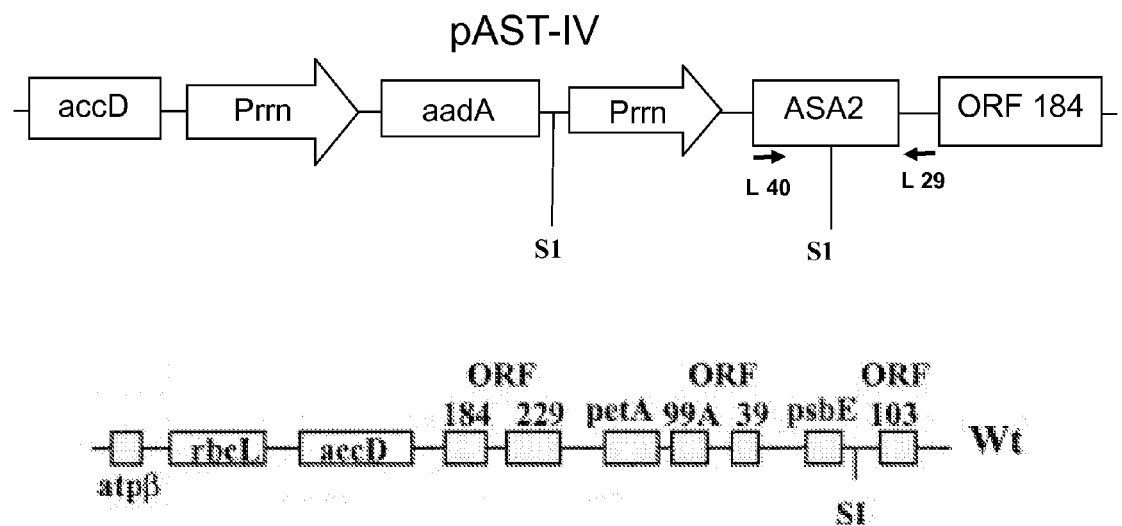
FIG. 8

| 1st Round of Selection | |
|---|---|
| 4-Methylindole 4-MI | 100; (200); 300 μM |
| 4-methyltrypthophan 4MT | (100); 200; 300 μM |
| 5-Methoxyindole 5MI | (100; 200); 300 μM |
| 5-Methyl-DL-tryptophan 5-MT | 100; 200; 300 μM |
| 7-Methyl-DL-tryptophan 7-MT | (100; 200); 300 μM |

| 2nd Round of Selection | |
|---|---|
| 4-Methylindole 4-MI | 75; (100); 125; 200; 300 μM |
| 4- methyltrypthophan 4MT | 50; 75; 100; (125) μM |

FIG. 14

| 2nd Round of Selection | |
|---|---|
| 4-Methylindole 4-MI | 75; 100; 125; 200; 300 μM |
| 4- methyltrypthophan 4MT | 50; 75; 100; 125 μM |
| 5-Methoxyindole 5MI | 50; 75; 100; 125 μM ? |
| 5-Methyl-DL-tryptophan 5-MT | 100; 125; 150 μM ? |
| 7-Methyl-DL-tryptophan 7-MT | 25; 50; 75; 100; 125; μM |

Hill 7MT 2nd Round of selection 1 wk 2 wks 3 wks 4 wks

| 2nd Round of Selection | |
|---|---|
| 4-Methylindole 4-MI | 75; (100); 125; 200; 300 µM |
| 4-methyltrypthophan 4MT | 50; 75; 100; (125) µM |
| 5-Methoxyindole 5MI | 50; 75; 100; 125 µM ? |

Hill 5MI 2nd Round of selection

Hill 5MT 2nd Round of selection

| Analog | Conc (μM) | WT | 763 |
|---|---|---|---|
| αMT | 15 | 2 | 3 |
| | 30 | 1 | 2 |
| | 100 | 0 | 0 |
| 7 MT | 75 | 3 | 4 |
| | 100 | 2 | 3 |
| | 150 | 0 | 2 |
| 4 MI | 15 | 1 | 3 |
| | 25 | 0 | 2 |
| | 50 | 0 | 0 |
| 5 HT | 50 | 3 | 3 |
| | 100 | 2 | 2 |
| | 300 | 2 | 2 |
| 4 FA | 30 | 1 | 3 |
| | 50 | 0 | 2 |
| | 150 | 0 | 0 |
| 6 FA | 30 | 1 | 1 |
| | 75 | 0 | 0 |
| | 150 | 0 | 0 |
| 6 FI | 25 | 2 | 3 |
| | 50 | 1 | 2 |
| | 100 | 0 | 1 |

FIG. 31

0= dead (brown or white)  1= very unhealthy (yellow brown)  2 = unhealthy (yellow green)  3= healthy (green)
4 = very healthy (green, normal growth)

US 7,847,152 B2

SEQUENCE LISTING

<160> NUMBER OF SEQ ID NOS: 19

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctaaaagcgg gaacttgatt ccgc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctgtacact tcaaatgggt cagc                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
accttagtga tctcgccttt cacg                                      24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcatatttct gcgggcataa gagt                                      24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtatcagcg cgaagtcttt                                           20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcggtgatga taatcggctg                                           20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taagaacggc catgcaccac c                                         21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaggaattga cggaagggca cca                                       23

<210> SEQ ID NO 9
<211> LENGTH: 1851
<212> TYPE: DNA
<213> ORGANISM: Nicotiana tabacum

<400> SEQUENCE: 9

```
atgcagtcgt tacctatctc ataccggttg tttccggcca cccaccggaa agttctgcca      60
ttcgccgtca tttctagccg gagctcaact tctgcacttg cgcttcgtgt ccgtacacta     120
caatgccgct gccttcactc ttcatctcta gttatggatg aggacaggtt cattgaagct     180
tctaaaagcg ggaacttgat tccgctgcac aaaaccattt tttctgatca tctgactccg     240
gtgctggctt accggtgttt ggtgaaagaa gacgaccgtg aagctccaag ctttctcttt     300
gaatccgttg aacctggttt tcgaggttct agtgttggtc gctacagcgt ggtggggct      360 caaccatcta tggaaattgt ggctaaggaa cacaatgtga ctatattgga ccaccacact     420
ggaaaattga cccagaagac tgtccaagat cccatgacga ttccgaggag tatttctgag     480
ggatggaagc ccagactcat tgatgaactt cctgatacct tttgtggtgg atgggttggt     540
tatttctcat atgacacagt tcggtatgta gagaacagga agttgccatt cctaagggct     600
ccagaggatg accggaacct tgcagatatt caattaggac tatacgaaga tgtcattgtg     660
tttgatcatg ttgagaagaa agcacatgtg attcactggg tgcagttgga tcagtattca     720
tctcttcctg aggcatatct tgatgggaag aaacgcttgg aaatattagt gtctagagta     780
caaggaattg agtctccaag gttatctccc ggttctgtgg atttctgtac tcatgctttt     840
ggaccttcat taaccaaggg aaacatgaca agtgaggagt acaagaatgc tgtcttacaa     900
gcaaaggagc acattgctgc aggagacata tttcaaatcg ttttaagtca acgctttgag     960
agaagaacat tgctgacccc atttgaagtg tacagagcat taagaattgt gaatccaagc    1020
ccatatatga cttacataca agccagaggc tgtattttag ttgcatcgag cccagaaatt    1080
ttgacacgtg tgaagaagag aagaattgtt aatcgaccac tggctgggac aagcagaaga    1140
gggaagacac ctgatgagga tgtgatgttg gaaatgcaga tgttaaaaga tgagaaacaa    1200
cgcgcagagc acatcatgct ggttgattta ggacgaaatg atgtaggaaa ggtgtcaaaa    1260
cctggttctg tgaatgtcga aaagctcatg agcgttgagc ggtattccca tgtgatgcac    1320
ataagctcca cggtctctgg agagttgctt gatcatttaa cctgttggga tgcactacgt    1380
gctgcattgc ctgttgggac cgtcagtgga gcaccaaagg taaaggccat ggagttgatt    1440
gatcagctag aagtagctcg gagagggcct tacagtggtg ggtttggagg catttccttt    1500
tcaggtgaca tggacatcgc actagctcta aggacgatgg tattcctcaa tggagctcgt    1560
tatgacacaa tgtattcata tacagatgcc agcaagcgtc aggaatgggt tgctcatctc    1620
caatccgggg ctggaattgt ggctgatagt aatcctgatg aggaacagat agaatgcgag    1680
aataaagtag ccggtctgtg ccgagccatt gacttggccg agtcagcttt tgtaaaggga    1740
agacacaaac cgtcagtcaa gataaatggt tctgtgccaa atctattttc aagggtacaa    1800
cgtcaaacat ctgttatgtc gaaggacaga gtacatgaga aagaaacta g              1851
```

<210> SEQ ID NO 10
<211> LENGTH: 377
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (339)..(377)

<400> SEQUENCE: 10

```
gaattcggct tggctccaag ttgttcaaga atagtggcgt tgagtttctc gacccttga      60 cttaggatta gtcagttcta tttctcgatg gggcggggaa gggatataac tcagcggtag    120
```

-continued

```
agtgtcacct tgacgtggtg gaagtcatca gttcgagcct gattatccct aagcccaatg      180
tgagtttttc tagttggatt tgctcccccg ccgtcgttca atgagaatgg ataagaggct      240
cgtgggattg acgtgagggg gcagggatgg ctatatttct gggagcgaac tccgggcgaa      300
tatgaagcgc atggatctcg agttgtaggg agggattt atg gct tct aaa agc ggg      356
                                         Met Ala Ser Lys Ser Gly
                                           1               5 aac ttg att ccg ctg cac aaa                                             377
Asn Leu Ile Pro Leu His Lys
            10
```

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Met Ala Ser Lys Ser Gly Asn Leu Ile Pro Leu His Lys
  1               5                  10
```

<210> SEQ ID NO 12
<211> LENGTH: 300
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (61)..(99)
<220> FEATURE:
<221> NAME/KEY: CDS
<222> LOCATION: (103)..(114)
<220> FEATURE:
<221> NAME/KEY: CDS
<222> LOCATION: (118)..(192)
<220> FEATURE:
<221> NAME/KEY: CDS
<222> LOCATION: (196)..(249)
<220> FEATURE:
<221> NAME/KEY: CDS
<222> LOCATION: (262)..(276)
<220> FEATURE:
<221> NAME/KEY: CDS
<222> LOCATION: (280)..(300)

<400> SEQUENCE: 12

```
aacgcttgga aatattagtg tctagagtac aaggaattga gtctccaagg ttatctcccg      60 gtt ctg tgg att tct gta ctc atg ctt ttg gac ctt cat taa cca agg        108
Val Leu Trp Ile Ser Val Leu Met Leu Leu Asp Leu His     Pro Arg
  1               5                  10                      15 gaa aca tga caa gtg agg agt aca aga atg ctg tct tac aag caa agg        156
Glu Thr     Gln Val Arg Ser Thr Arg Met Leu Ser Tyr Lys Gln Arg
                 20                  25                      30 agc aca ttg ctg cag gag aca tat ttc aaa tcg ttt taa gtc aac gct        204
Ser Thr Leu Leu Gln Glu Thr Tyr Phe Lys Ser Phe     Val Asn Ala
            35                  40                      45 ttg aga gaa gaa cat ttg ctg acc cat ttg aag tgt aca gag cat            249
Leu Arg Glu Glu His Leu Leu Thr His Leu Lys Cys Thr Glu His
            50                  55                  60 taagaattgt ga atc caa gcc cat ata tga ctt aca tac aag cca gag gct      300
               Ile Gln Ala His Ile     Leu Thr Tyr Lys Pro Glu Ala
                65                              70
```

```
<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Trp Ile Ser Val Leu Met Leu Leu Asp Leu His
 1               5                  10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Arg Glu Thr
 1

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Val Arg Ser Thr Arg Met Leu Ser Tyr Lys Gln Arg Ser Thr Leu
 1               5                  10                  15

Leu Gln Glu Thr Tyr Phe Lys Ser Phe
            20                  25

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Asn Ala Leu Arg Glu Glu His Leu Leu Thr His Leu Lys Cys Thr
 1               5                  10                  15

Glu His

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Gln Ala His Ile
 1               5

<210> SEQ ID NO 18
<211> LENGTH: 7
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Thr Tyr Lys Pro Glu Ala
  1               5

<210> SEQ ID NO 19
<211> LENGTH: 1874
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19
ctaaaagcgg gaacttgatt ccgctgcaca aaaccatttt ttctgatcat ctgactccgg      60
tgctggctta ccggtgtttg gtgaaagaag acgaccgtga agctccaagc tttctctttg    120
aatccgttga acctggtttt cgaggttcta gtgttggtcg ctacagcgtg gtggggctc    180 aaccatctat ggaaattgtg gctaaggaac acaatgtgac tatattggac caccacactg    240
gaaaattgac ccagaagact gtccaagatc ccatgacgat tccgaggagt atttctgagg    300
gatggaagcc cagactcatt gatgaacttc ctgatacctt tgtggtgga tgggttggtt     360 atttctcata tgacacagtt cggtatgtag agaacaggaa gttgccattc ctaagggctc    420
cagaggatga ccggaaccct tgcagatatt caattaggact atacgaagat gtcattgtgt   480
ttgatcatgt tgagaagaaa gcacatgtga ttcactgggt gcagttggat cagtattcat    540
ctcttcctga ggcatatctt gatgggaaga acgcttgga atattagtg tctagagtac      600 aaggaattga gtctccaagg ttatctcccg gttctgtgga tttctgtact catgcttttg    660
gaccttcatt aaccaaggga acatgacaa gtgaggagta caagaatgct gtcttacaag     720
caaaggagca cattgctgca ggagacatat ttcaaatcgt tttaagtcaa cgctttgaga    780
gaagaacatt tgctgaccca tttgaagtgt acagagcatt aagaattgtg aatccaagcc    840
catatatgac ttacatacaa gccagaggct gtattttagt tgcatcgagc ccagaaattt    900
tgacacgtgt gaagaagaga agaattgtta atcgaccact ggctgggaca agcagaagag    960
ggaagacacc tgatgaggat gtgatgttgg aaatgcagat gttaaaagat gagaaacaac   1020
gcgcagagca catcatgctg gttgatttag gacgaaatga tgtaggaaag gtgtcaaaac   1080
ctggttctgt gaatgtcgaa aagctcatga gcgttgagcg gtattcccat gtgatgcaca   1140
taagctccac ggtctctgga gagttgcttg atcatttaac ctgttgggat gcactacgtg   1200
ctgcattgcc tgttgggacc gtcagtggag caccaaaggt aaaggccatg gagttgattg    1260
atcagctaga agtagctcgg agagggcctt acagtggtgg gtttggaggc atttcctttt   1320
caggtgacat ggacatcgca ctagctctaa ggacgatggt attcctcaat ggagctcgtt    1380
atgcacaaat gtattcatat acagatgcca gcaagcgtca ggaatgggtt gctcatctcc    1440
aatccggggc tggaattgtg gctgatagta atcctgatga ggaacagata gaatgcgaga   1500
ataaagtagc cggtctgtgc cgagccattg acttggccga gtcagctttt gtaagggaa    1560 gacacaaacc gtcagtcaag ataaatggtt ctgtgccaaa tctatttca agggtacaac    1620 gtcaaacatc tgttatgtcg aaggacagag tacatgagaa aagaaactag cgaatatgaa    1680
gatgtacata aattctaaag tggttttctt gttcagttta atctttact ggattgagac    1740
```

```
tgtagttgct gaagatagtt gtttagaatg accttcattt tggtgttcct gaaaggacag    1800
tgcacatata tagcaaattg atcaaatgtt taatccttgt atgcgggtga gaatcaatgc    1860
catcagcaat ttgg                                                      1874
```

USE OF TRYPTOPHAN INDOLE AND ANTHRANILATE ANALOGS AS PLANT TRANSFORMATION SELECTION AGENTS

This application claims priority to U.S. Ser. No. 60/806,280 filed Jun. 30, 2006, the disclosure of which is hereby incorporated by reference.

TECHNICAL FIELD

The present disclosure relates to the field of plant transformation using selectable agents.

BACKGROUND

Selection of transformed plants and plant cells in vitro often poses difficulties. Some of the technical challenges for selection include the clumpy nature of plant cell cultures; difficulty of single cells or protoplasts to grow and form clones; slow cell growth and polyploidy of the cells. Despite these problems a large number of successful selection experiments have been carried out to produce genetically engineered plants and cells for improving crop plants.

There are several types of in vitro selection techniques that can be used to obtain cells containing a trait of interest. These include selection for growth, selection for valuable compound production, auxotroph selection and resistance selection. Selection for resistance to an agent is generally the preferred kind of selection to screen for transformed cells or plants. Some of the examples include selection agents such as antibiotics and herbicides.

Selection for amino acid analog resistance in plants has been pursued for a number of years. A primary focus of this research has been directed to the enzyme anthranilate synthase (AS). AS catalyzes the conversion of chorismate into anthranilate, the first reaction leading from the common aromatic amino acid (shikimate) pathway toward the biosynthesis of tryptophan (Trp). As a branch-point enzyme in the synthesis of aromatic amino acids, AS plays a key role in the diversion of chorismate into Trp and indolic secondary compound biosynthesis.

In microbes, AS usually consists of two non-identical subunits, referred to as the alpha subunit (component I) and the beta subunit (component II). Component I can convert chorismate to anthranilate in the presence of high levels of ammonia (ammonia-dependent AS activity), whereas component II is responsible for the use of glutamine (hereinafter referred to as "Gln") as the amino donor.

To investigate regulation of the Trp pathway, toxic analogs of Trp have been used in metabolic studies of plant cell cultures and as a tool to select mutants. Many of these studies have been conducted with the growth inhibitor 5-methyltryptophan (5MT). In addition, 5-methylanthranilate was used to isolate plant auxotrophic mutants defective in three different genes, trp1, trp2, and trp3. 5MT has also been used to identify mutants of *Chlamydomonas reinhardtii*. Mutants resistant to 5MT or alpha-methyltryptophan (αMT) were reported in *Arabidopsis thaliana* and other plants. The specificity of selection with these analogs has not been systematically investigated.

A feedback-insensitive AS gene (ASA1 mutant) has been identified by selection of mutagenized *Arabidopsis* seeds resistant to 6-methylanthranilate. A 5-methyltryptophan resistant *Nicotiana tabacum* anthranilate synthase gene (ASA2) was reported in U.S. Pat. No. 6,563,025 B1, the disclosure of which is hereby incorporated by reference.

One of the methods for developing transgenic plants is to transform plant cells in tissue culture with a plasmid or an expression cassette containing a promoter and selectable marker, which also contains a gene of interest. The gene of interest expresses the desired trait in the regenerated transgenic plant.

In plants, plastids generally differentiate into several forms based on the function they perform. For example, undifferentiated plastids (proplastids) may develop into amyloplasts (starch storage), chloroplasts (photosynthesis), etioplasts (chloroplasts that have not been exposed to light), elaioplasts (store fat), chromoplasts (pigment synthesis and storage), and leucoplasts (monoterpene synthesis). Each plastid contains multiple copies of the circular 75-250 kilo base plastid genome. The number of genome copies per plastid varies from more than 100 in rapidly dividing cells to about 20 or fewer in mature cells. The plastid genome contains about 100 genes encoding ribosomal and transfer ribonucleic acids (rRNAs and tRNAs) as well as proteins involved in photosynthesis and plastid gene transcription and translation.

Plastid transformation utilizes particle bombardment to deliver a transgene into the plastids where the integration is generally by homologous recombination using homologous (identical) plastid DNA sequences (generally about 1-4 kb long on each end) flanking the transgenes. The flanking sequences act as anchoring regions to initiate site-specific gene targeting in the plastid genome and homologous recombination during plastid transformation.

A plant-derived gene, such as an AS gene encoding an enzyme that is highly resistant to an amino acid analog or other agent, is an ideal selectable marker for the production of transgenic plants, because it minimizes the environmental concern regarding the use of non-plant resistance genes in plants for selection. Traditional selectable markers that are not of plant origin include nptII, which encodes kanamycin resistance.

Because many of the methods for inserting DNA into plants are inefficient and result in large numbers of plants of which only a tiny proportion are transformed, need exists for a robust plant-derived selection system. Selectable marker genes are therefore a pre-requisite for almost all of the current methods of plant transformation.

SUMMARY

Novel selection agents and methods for plant transformation using the ASA2 gene are disclosed. Methods are described using tryptophan analogs, indole analogs, and mixtures thereof as agents for selecting plant cells that have been transformed with an ASA2 gene or a fragment thereof, where the ASA2 gene encodes a feedback-insensitive form of AS.

A method for selecting a transformed plant cell includes the steps of:

(a) expressing a nucleic acid sequence encoding a feedback insensitive anthranilate synthase (ASA2) or a functional fragment thereof in a plant cell by introducing the nucleic acid sequence in the plant cell; and (b) selecting the plant cell that expresses the nucleic acid sequence by contacting the plant cell with a medium containing a tryptophan or an indole analog, wherein the tryptophan or the indole analog is at a concentration effective to inhibit the growth of a plant cell that does not express the nucleic acid sequence.

Suitable tryptophan analogs include 6-methyltryptophan, 7-methyltryptophan, and 4-fluorotryptophan, or a combination thereof, wherein the tryptophan analog is at a concentration effective to inhibit the growth of a plant cell that does not express the nucleic acid sequence.

Suitable indole analog selected from the group consisting of 4-fluoroindole, 5-fluoroindole, 6-fluoroindole, 6-aminoindole, 4-methylindole, 5-methoxyindole, and 7-methoxyindole, or a combination thereof, wherein the indole analog is at a concentration effective to inhibit the growth of a plant cell that does not express the nucleotide sequence.

The vector or expression cassette that harbors the ASA2 functional sequence or fragments thereof may also include a nucleotide sequence that encodes a gene of interest. The nucleic acid sequence is introduced by plastid transformation or by nuclear transformation. The nucleic acid sequence is introduced by homologous recombination for plastid transformation. The nucleic acid sequence is usually introduced by particle bombardment.

A nucleic acid encoding ASA2 or functional fragments thereof is operably linked to a promoter functional in a plant cell. ASA2 nucleic acid or functional fragments thereof are operably linked to a promoter functional in a plastid. In an aspect, the gene of interest is under the control of plastid promoter.

The gene of interest may confer one or more of the traits selected from disease resistance, increased biomass, reduced lignin content, higher nutritive value, stress tolerance, pest resistance, altered flowering time, altered maturity, altered morphology, compound production, and vaccine production.

A method for increasing the tryptophan content in a plant includes the steps of:

(a) expressing a nucleic acid sequence encoding a feedback insensitive anthranilate synthase (ASA2) in a plant cell;

(b) selecting the plant cell that expresses the nucleic acid in a medium containing a tryptophan analog for example 6-methyltryptophan, 7-methyltryptophan, and 4-fluorotryptophan, or a combination thereof, or an indole analog selected from the group of 4-fluoroindole, 5-fluoroindole, 6-fluoroindole, 6-aminoindole, 4-methylindole, 5-methoxyindole, and 7-methoxyindole, or a combination thereof, wherein the analog is at a concentration effective to inhibit the growth of a plant cell that does not express the nucleotide sequence; and (c) regenerating a plant from the plant cell, wherein the cells of the plant express the anthranilate synthase and thereby increase the tryptophan content in the cells of the differentiated plant compared to the tryptophan content in the cells of the plant that does not express the feedback insensitive anthranilate synthase (ASA2).

A method of selecting transformed plastids includes the steps of:

(a) expressing a nucleic acid sequence encoding a feedback insensitive anthranilate synthase (ASA2) in a plant cell; and (b) selecting the plant cell that expresses the nucleic acid sequence by contacting the plant cell with a medium containing a tryptophan analog for example alpha-methyltryptophan, 6-methyltryptophan, 7-methyltryptophan, and 4-fluorotryptophan, or a combination thereof, or an indole analog for example 4-fluoroindole, 5-fluoroindole, 6-fluoroindole, 6-aminoindole, 4-methylindole, 5-methoxyindole, and 7-methoxyindole, or a combination thereof, wherein the analog is at a concentration effective to inhibit the growth of a plant cell that does not express the nucleotide sequence.

A method for obtaining a homoplastomic plant includes the steps of:

(a) transforming a plastid with a nucleic acid sequence encoding a feedback insensitive anthranilate synthase (ASA2) or a functional fragment thereof in a plant cell;

(b) selecting the plant cell that expresses the nucleic acid sequence by contacting the plant cell with a medium containing a tryptophan analog for example, alpha-methyltryptophan, 6-methyltryptophan, 7-methyltryptophan, and 4-fluorotryptophan, or a combination thereof, or an indole analog selected from the group of 4-fluoroindole, 5-fluoroindole, 6-fluoroindole, 6-aminoindole, 4-methylindole, 5-methoxyindole, and 7-methoxyindole, or a combination thereof, wherein the analog is at a concentration effective to inhibit the growth of a plant cell that does not express the nucleotide sequence; and (c) obtaining a homoplastomic plant by one or more successive steps of selection using the analogs listed in step (b).

The concentration of the tryptophan analog may range in concentration from 1 µM to about 1 mM and to about 10 mM; the concentration of the indole analog ranges in concentration from 1 µM to about 1 mM and up to 10 mM.

A homoplastomic plant regenerated from a transformed plant cell, wherein the transformed plant cell includes a nucleic acid sequence encoding a feedback insensitive anthranilate synthase (ASA2) or a functional fragment thereof as the sole selection marker is disclosed.

The homoplastomic plant may further include a gene of interest that confers one or more of the traits selected from disease resistance, increased biomass, reduced lignin content, increased nutritive value, stress tolerance, and pest resistance.

BRIEF DESCRIPTION OF THE DRAWINGS

FIG. 3 shows a schematic illustration of plasmid pAST-IV. The Prrn-ASA2 expression cassette was flanked by the accD and ORF184 of the tobacco plastid region to obtain the vector pAST-IV.

FIG. 4 shows the location of the primers L40 and L39 used for amplification of a 815 by fragment of the ASA2 gene. 4A. DNA: SEQ ID NO: 10 encodes PRT: SEQ ID NO: 11; 4B. DNA: SEQ ID NO: 12 encodes PRTs: SEQ ID NOS 13-18; primer disclosed as SEQ ID NO: 2.

FIG. 5 shows PCR amplification with ASA2 specific primers L39 (SEQ ID NO: 2) and L40 (SEQ ID NO: 1). M: DNA marker; 26-F: transgenic lines; WT: wild type cv. Havana; P: p-ASTIV plasmid (SEQ ID NO: 19); B: blank control.

FIG. 7 shows northern-blot hybridization was carried out to determine the expression of the Prrn-ASA2 gene in the transformed plants. The transplastomic plants showed 2.5- and 7.5-kb bands for the pAST-IV plants. The 2.5-kb transcripts in the pAST-IV plants end in the intergenic region between accD and ORF184, whereas the 7.5-kb mRNA apparently includes sequences from other downstream genes. This indicates that the pAST-IV plants express a 7.5-kb mRNA in which the ASA2 gene is a part of the transcribed operon that apparently includes seven putative genes (ORF184, ORF229, petA, ORF99A, ORF39, psbE, and ORF103).

FIG. 8 is a Southern blot hybridization with genomic DNA digested with SacI and hybridized with an 815 kb ASA2 probe M: DNA ladder (Invitrogen); Lanes 26 through F: individual transplastomic plants, WT: Wild-type. When hybridized to an 815 kb ASA2 probe, the SacI-digested DNA blot reveals two bands at 1.8 and 10 kb for the plastid transgenic lines (FIG. 10). The 1.8-kb band is much stronger because the AS probe covers most of the fragment. No signal was detected in the wild-type plant.

FIG. 14 shows concentration ranges used for various analogs in the $1^{st}$ and $2^{nd}$ round screening. The concentration indicated in circles in the drawings disclosed herein, are optimal concentrations after either the first round of selection or the second round of screening based on growth inhibition.

FIG. 24 5MI $2^{nd}$ round of selection for Hi II cultivar.

FIG. 31 shows qualitative results for various analogs and their effects on soybean embryogenic culture growth.

DETAILED DESCRIPTION

Methods and compositions to increase the efficiency of a selection system with the ASA2 gene are disclosed. Seedling growth and leaf callus formation inhibition experiments on media with different tryptophan (Trp) and indole analogs have resulted in the identification of novel Trp and indole analogs for use in plant transformation. Several of the analogs listed in Table 1 are suitable for use as selection agents. Analogs 7-MT and 4-MI exhibited enhanced selection properties.

Figure 39:
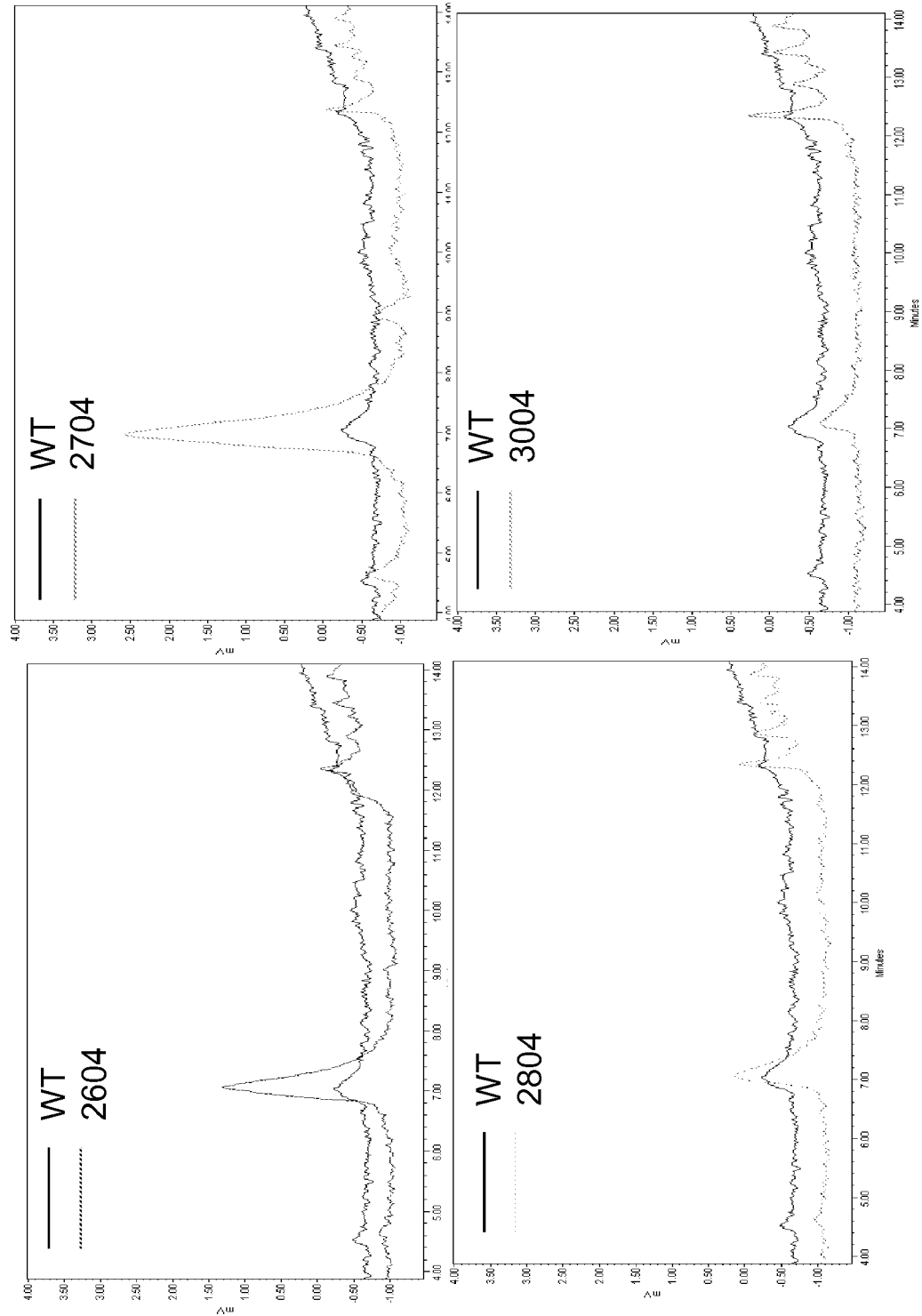
FIG. 39 shows free tryptophan levels of ASA2 expressing transgenic lines 2604, 2704, 2804, and 3004 as compared to wild-type tobacco.
Figure 40:
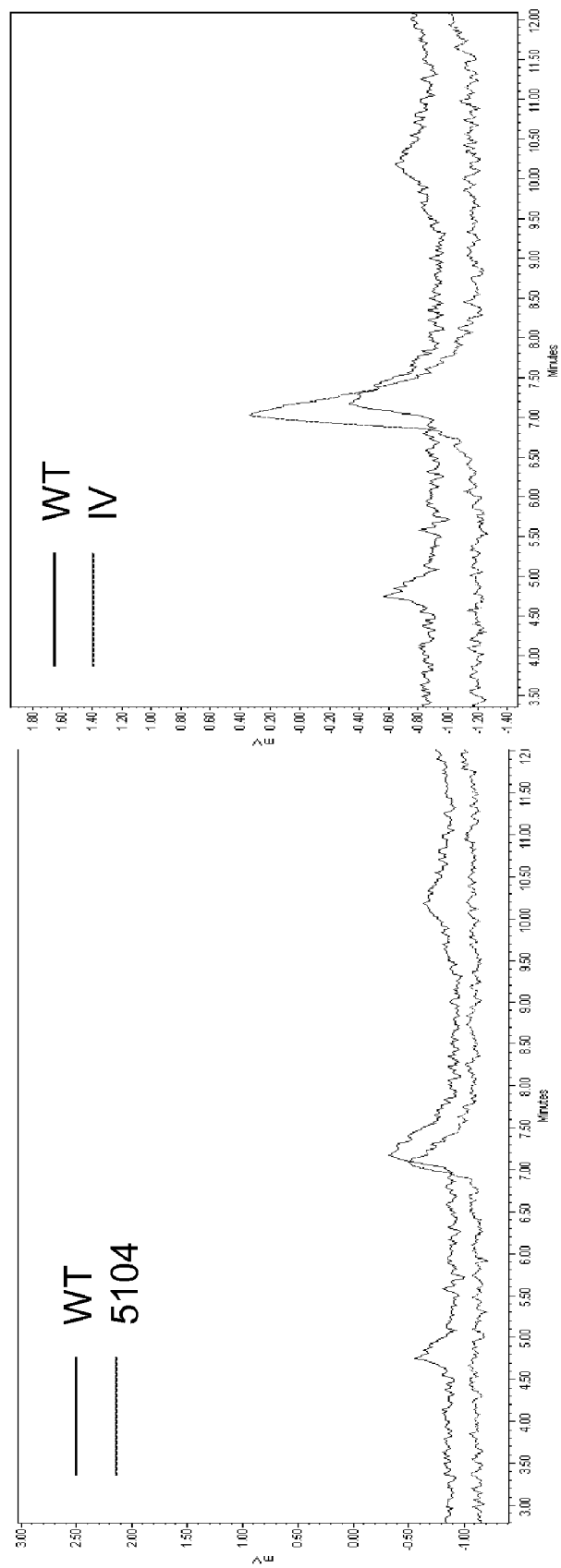
FIG. 40 shows free tryptophan levels of ASA2 expressing transgenic lines 5104 and IV as compared to wild-type tobacco.

The anthranilate synthase alpha subunit (ASA2) gene encodes the tobacco tryptophan (Trp) biosynthesis control enzyme and imparts resistance to toxic Trp and indole analogs since it is feedback insensitive. The Trp analogs are toxic since they are able to mimic the specific inhibitory effect (feedback effect) of tryptophan on the AS. A sensitive enzyme fails to discriminate completely between its normal feedback inhibitor, Trp, and an analog. If the feedback insensitive AS is expressed, then the cells are resistant to the analogs, and can be selected for. Seedling growth inhibition and leaf callus formation were studied using either the wild-type (WT) tobacco or the 5MT resistant transgenic plants, on medium supplemented with various concentrations of different Trp and indole analogs. The feedback-insensitive ASA2 cDNA gene, isolated from the 5MT-resistant tobacco cell line AB15-12-1 (Song et al., 1998), was placed under the control of CaMV35S promoter in the binary vector C2ASA2. Tobacco plants were transformed by A. tumefaciens. Regenerated primary transformants were selected either on 300 μm 4MI or 400 μm 7MT then analyzed by PCR, Southern and northern blot analysis. The AS, the holoenzyme activity and the free Trp content were measured in leaf extracts of shoot cultures from both transgenic lines and WT Xanthi. Most of the transgenic lines selected show ASA2 overexpression and increase in free Trp content (FIGS. 39-40).

Anthranilate synthase (AS) includes two subunits: α and β units. From a 5MT resistant tobacco plant, a feedback insensitive α-subunit (ASA2) gene was isolated, which allows transformed plants to survive in the presence of Trp analogs and indole analogs. In both indole and Trp analogs, a sensitive enzyme fails to discriminate completely between its normal feedback inhibitor, tryptophan, and an analog. Indole analogs are converted to tryptophan analogs by endogenous tryptophan synthase activity. If the feedback insensitive AS is expressed, then the cells are resistant to the analogs. Under normal cellular regulation, the analogs result in feedback inhibition of the Trp synthesis pathway controlled by AS resulting in greatly reduced Trp synthesis and poor survival as Trp is an essential amino acid.

The feedback-insensitive ASA2 cDNA gene, isolated from the 5MT-resistant tobacco cell line AB15-12-1, was placed under the control of the modified plastid 16S rRNA operon promoter (Prrn). The Prrn-ASA2 expression cassette was flanked by the accD and ORF184 of the tobacco plastid region to obtain the vector pAST-IV.

ASA2 is a suitable selectable marker for plastid transformation of a gene of interest and for selection by Trp and indole analogs in growth medium. ASA2 is also a suitable selectable marker for nuclear transformation and for selection by Trp and indole analogs in growth medium. Transformation of plastids generally requires particle bombardment, such as a gold bombardment procedure. Using a native plant gene (e.g., ASA2) as a selectable marker and novel selective agents such as Trp and indole analogs are advantageous to avoid the introduction of antibiotic or herbicide resistant genes that could be transferred to microbes or other plant pathogens or weeds with undesirable consequences. The use of Trp and indole analogs including 7MT and 4MI expands the availability of selection agents suitable for plant transformation.

Anthranilic acid and anthranilate analogs also are suitable selection agents to screen transformants that express the ASA2 gene. Anthranilic acid and anthranilate analogs work similar to indole analogs due to the fact that they are converted to tryptophan by enzymes present in the plant cell.

The use of ASA2 gene or functional fragments thereof in combination with the selection agents disclosed herein are applicable to any plant species that is capable of being genetically transformed including tobacco, corn, soybean, *Arabidopsis*, tomato, wheat, rice, barley.

Plastid transformation of tobacco leaf discs was carried out with the vector pAST-IV. Green calli and shoots resistant to either 7-MT or 4-MI were obtained and subjected to three additional rounds of selection. PCR testing and Southern-blot analysis were performed to confirm the presence of the transgene and the homoplastomic condition. Free Trp and AS activity were measured. The Prrn-ASA2 cassette was expressed effectively in plants of *N. tabacum* allowing the selection of transformants using either Trp or Indole analogs disclosed herein.

Homoplastomic plants that contain the ASA2 gene or a functional derivative thereof as a selectable marker, and that do not contain a non-plant based selectable marker, are desirable for several reasons. For example, non-plant based marker genes are sometimes disfavored among some consumers of genetically modified crops; use of ASA2 gene as a marker presents lower environmental risks of antibiotic resistance; and minimizes allergenic response in genetically modified crops. A homoplastomic plant that contains a plant based selectable marker (e.g., ASA2) as the sole selectable marker is desirable.

Although the present disclosure uses ASA2 from *N. tabacum* as an example of an AS gene for use with the analogs disclosed herein, one skilled in the art would realize that the selection agents disclosed herein are applicable to any gene or fragment encoding the feedback-insensitive form of the AS enzyme, and preferably a *Nicotiana* AS gene. As used herein, a "feedback-insensitive form of the AS enzyme" is an AS that is inhibited to lesser extent by free Trp or an amino acid analog of Trp or indole analog, as compared to the corresponding "wild-type" or native AS of the species. The indole analogs are generally converted to Trp analogs within the plant or cell culture by endogenous tryptophan synthase activity.

Plastid transformation refers to introducing one or more nucleic acid molecules inside a plastid into the plastid chromosome. Generally, the selectable marker is under the control of a constitutive promoter or a suitable promoter capable of expressing in plastids.

The ASA2 functional gene or functional fragments or subunits thereof may be operatively associated with any suitable promoter. Some of the known promoters known in the include CaMV 35S, cassava vein mosaic virus, ubiquitin, and actin promoters. Other suitable promoters include ASA2 promoter, viral coat protein promoter, a plant tissue-specific promoter, a monocot promoter, a CaMV 19S promoter, a nos promoter, an Adh promoter, a sucrose synthase promoter, a tubulin promoter, a cab promoter, a PEP Case promoter, a mannopine synthase promoter, a soybean vegetative storage protein promoter, and a root-cell promoter. The promoter may be inducible. The inducible promoter may promote the expression the ASA2 gene in cultured cells or tissue or in plant. Inducible promoters known in the art include auxin, tetracycline, copper, ethanol, and glucocorticoid inducible promoters.

The ASA2 gene or its functional fragment and a gene of interest may be expressed in a number of suitable ways. First, for example, the gene of interest and the ASA2 gene may be operatively associated with the same promoter that drives the ASA2 gene or its fragments thereof. Second, the gene of interest and the ASA2 gene may be driven by different and separate promoters. For example, the ASA2 gene or its functional fragment may be expressed by a constitutive promoter, whereas the gene of interest may be expressed by a tissue specific promoter or may not be operatively associated with the same promoter of ASA2 functional fragment. One of the rationales underlying the independent expression strategy is to independently control and regulate the expression of a functional ASA2 gene fragment and the gene of interest depending on the transformation system used, desired trait of interest, and the nature of the gene of interest. Thus, one skilled in the art may selectively induce expression, in the transformed cells or plant of the ASA2 gene, but not the desirable gene, until it is desired to express the gene of interest in the regenerated plant or cell culture. Conversely, it may be desirable to express ASA2 or its functional fragment during the selection process and not in the regenerated plant. For example, if an ASA2 promoter (native promoter) or another inducible promoter is operatively associated with the ASA2 gene, it would be useful for controlling the ASA2 gene expression to select for the transformed cultured cells, but the marker is not expressed in plants regenerated from these transformed cells. Meanwhile, because the gene of interest is operatively associated with another promoter, this promoter allows the expression of the gene of interest in the transformed cultured cells and/or transformed plants. One skilled in the art would realize that one or more desirable gene(s) and promoter(s) may be used in the construct.

For example, the ASA2 sequence and/or the desirable gene may be inserted into a DNA construct such as a plant expression vector. The term "recombinant vector" and "recombinant expression vector" refers to any suitable plant vectors or binary vectors including a plasmid, virus or other vehicle known in the art that has been manipulated by insertion or incorporation of ASA2 nucleic acid sequence or a functional derivative thereof. An expression vector generally contains an origin of replication, a promoter, as well as selectable marker genes, which allow phenotypic selection of the transformed cells.

The following examples are intended for purposes of illustration only and should not be construed as in any sense limiting the scope of the disclosure.

EXAMPLES

Example 1

Seedling Growth and Leaf Callus Formation Inhibition

This example demonstrates that the Trp and Indole analogs disclosed herein exhibit inhibitive properties on wild-type plants compared to the analog resistant plants. The concentrations listed in Table 1 are for illustrative purposes and should not be construed as a limited range. Seedling growth inhibition was studied by placing a total of 45 surface-sterilized seeds of either the wild-type (WT) tobacco (*Nicotiana tabacum* cv. Petit Havana SR1) or the ASA2 expressing transgenic plants previously obtained (Zhang et al., 2001), on Murashige-Skoog medium supplemented with 3% sucrose, vitamins, 0.8% agar and various concentrations of the different analogs (see Table 1). Seed germination and root formation were measured after 2 weeks, at 28° C. under fluorescent light. The analogs listed in Table 1 were obtained from Sigma-Aldrich (St. Louis, Mo.) or Acros Organics (Morris Plains, N.J.).

TABLE 1

| | Concentrations |
|---|---|
| Trp analogs | |
| 5-methyltrypthophan (5MT) | 10; 30; 100 and 300 µm |
| α- methyltrypthophan (αMT) | 1; 3; 10; 30; 100; 300 µm |
| 4- methyltrypthophan (4MT) | 10; 30; 100 and 300 µm |
| 5-hydroxyl-L-tryptophan (5HT) | 10; 30; 100 and 300 µm |
| 7- methyl-DL-tryptophan (7MT) | 10; 30; 100; 300; 400 and 500 µm |
| 6- methyl-DL-tryptophan (6MT) | 10; 30; 100; 300; 600 and 1000 µm |
| DL-4-fluorotryptophan (4FT) | 10; 30; 100 and 300 µm |
| DL-5-fluorotryptophan (5FT) | 10; 30; 100 and 300 µm |
| DL-6-fluorotryptophan (6FT) | 10; 30; 100 and 300 µm |
| Indole analogs | |
| 6-Fluoroindole (6FI) | 10; 30; 50; 70; 100 and 300 µm |
| 4-Fluoroindole (4FI) | 10; 20; 30; 100 and 300 µm |
| 5-Fluoroindole (5FI) | 10; 30; 100; 150; 200 and 300 µm |
| 5-Methoxyindole (5MI) | 10; 30; 100 and 300 µm |
| 7-Methoxyindole (7MI) | 10; 30; 100 and 300 µm |
| 6-Aminoindole | 10; 30; 100 and 300 µm |
| 4-Methylindole (4MI) | 10; 30; 100; 300 and 600 µm |

Leaf callus formation was studied on the nutrient medium described herein using a total of 30 leaf discs at 28° C. under fluorescent light. After 2 weeks, callus formation was measured and after 4 weeks shoot production was recorded.

Figure 1:
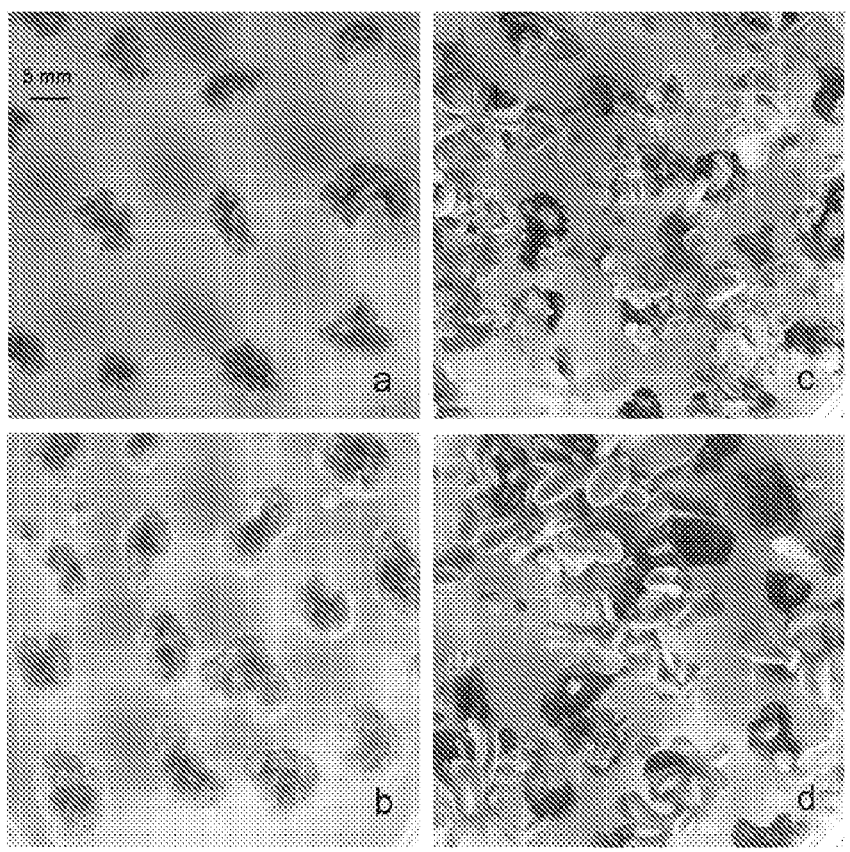
FIG. 1 shows photographs of leaf callus formation inhibition. At 300 µm 4MI and 300 µm 7MT, the callus production of the wild-type showed greater inhibition (FIGS. 1a & b). In contrast, the growth the 5-MT resistant plants was not affected by treatment with 300 µm 4MI (FIG. 1c) or 300 µm 7MT (FIG. 1d).
Figure 2:
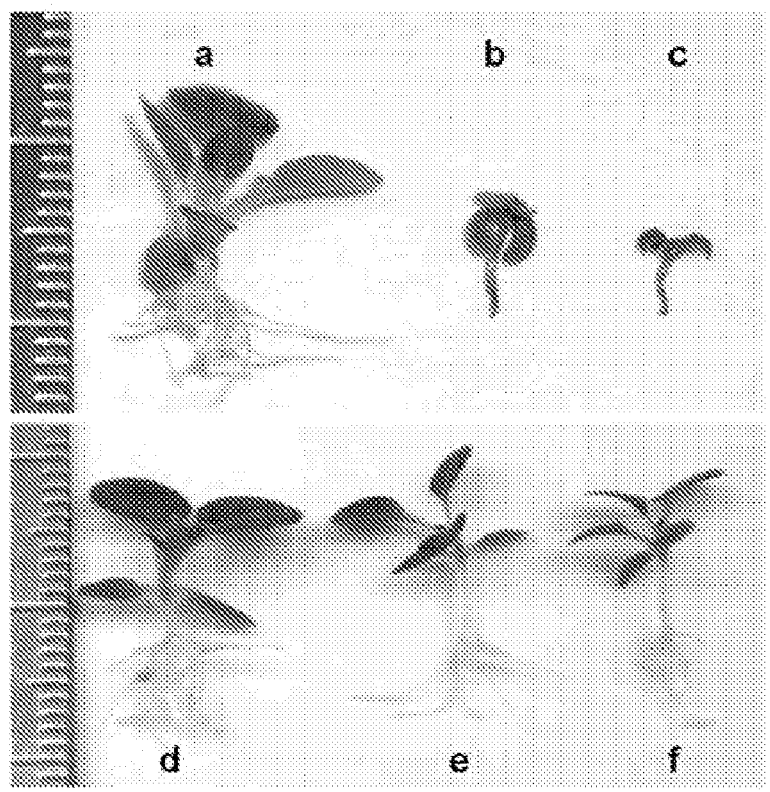
FIG. 2 shows seedling growth inhibition test: WT seedlings on rooting medium without analog (a) with 75 µm 4MI (b) and 75 µm 7MT (c) after 2 weeks. Six weeks old ASTIV line seedlings on rooting medium without analog (d) or on medium with concentrations of 4MI or 7MT tested (e and f). Marks of the ruler are mm.

The wild-type plant germination and callus formation were inhibited by treatment with 300 µm 4MI and 300 µm 7MT respectively. At 300 µm 4MI and 300 µm 7MT, the callus production of the wild-type showed greater inhibition (FIGS. 1*a* & *b*) and the growth of the seedlings/roots was completely inhibited (FIGS. 2*a* & *b*). In contrast, the growth of the ASA2 expressing plants was not affected by treatment with 300 µm 4MI (FIGS. 1*c* & 2*c*) or 300 µm 7MT (FIGS. 1*d* & 2*d*).

Thus, the data demonstrate that 7MT and 4MI are effective selective agents listed for use as suitable selection agents to screen for plants or plant cells harboring a feedback insensitive form of an AS gene.

Example 2

Plastid Transformation and Selection Using Trp and Indole Analogs

The feedback-insensitive ASA2 cDNA, isolated from the 5MT-resistant tobacco cell line AB15-12-1, was placed under the control of the modified plastid 16S rRNA operon promoter (Prrn). The Prrn-ASA2 expression cassette was flanked by the accD and ORF184 of the tobacco plastid region to obtain the vector pAST-IV (FIG. 3).

DNA preparation, precipitation onto gold particles, and bombardment were performed as described previously (Svab & Maliga P, 1993) using 0.6 µm gold particles (Bio-Rad, Hercules, Calif.) as micro projectiles. Any suitable particle bombardment procedure can be used. Briefly, the plasmid containing the marker gene and a gene of interest are coated onto gold or tungsten microparticles. The coated particles are air dried and loaded on to a particle gun for particle bombardment into the desired tissue. *Nicotiana tabacum* cv. Havana was used in the experiments. Green calli and shoots resistant to either 7-MT or 4-MI were obtained after 6-8 wks of selection on RMOP medium (Svab et al., 1990) and subjected to three additional rounds of selection for the homoplastomic condition.

Example 3

Screening of Transformed Plants

Genomic DNA was extracted using a standard Cetyl Trimethyl Ammonium Bromide (CTAB) protocol from young fully expanded leaves. Briefly, plant material is ground and the DNA is extracted using the CTAB buffer through standard precipitation procedures. PCR was carried out to identify the right insertion of the ASA2 gene, with Taq DNA polymerase, for 30 cycles at 94° C. for 45 s, 55° C. for 45 s and 72° C. for 1.30 min.

The primers used for amplification of a 815 by fragment of the ASA2 gene were L 40 5'-CTAAAAGCGGGAACT-TGATTCCGC-3' (SEQ ID NO: 1) located at the beginning of the mature ASA2 coding region and L39 5'-TCTGTACACT-TCAAATGGGTCAGC (SEQ ID NO: 2) located in the middle of the ASA2 coding region (FIG. 4). The primer for RaadA is 5'-ACC TTA GTG ATC TCG CCT TTC ACG-3' (SEQ ID NO: 3).

To verify the correct site of integration into the plastid genome PCR was carried out with primers L40 and L 29 5'-TCATATTTCTGCGGGCATAAGAGT-3' located upstream of the plastid genome ORF 184 and a 2.1 kb fragment was expected (FIG. 4).

Figure 6:
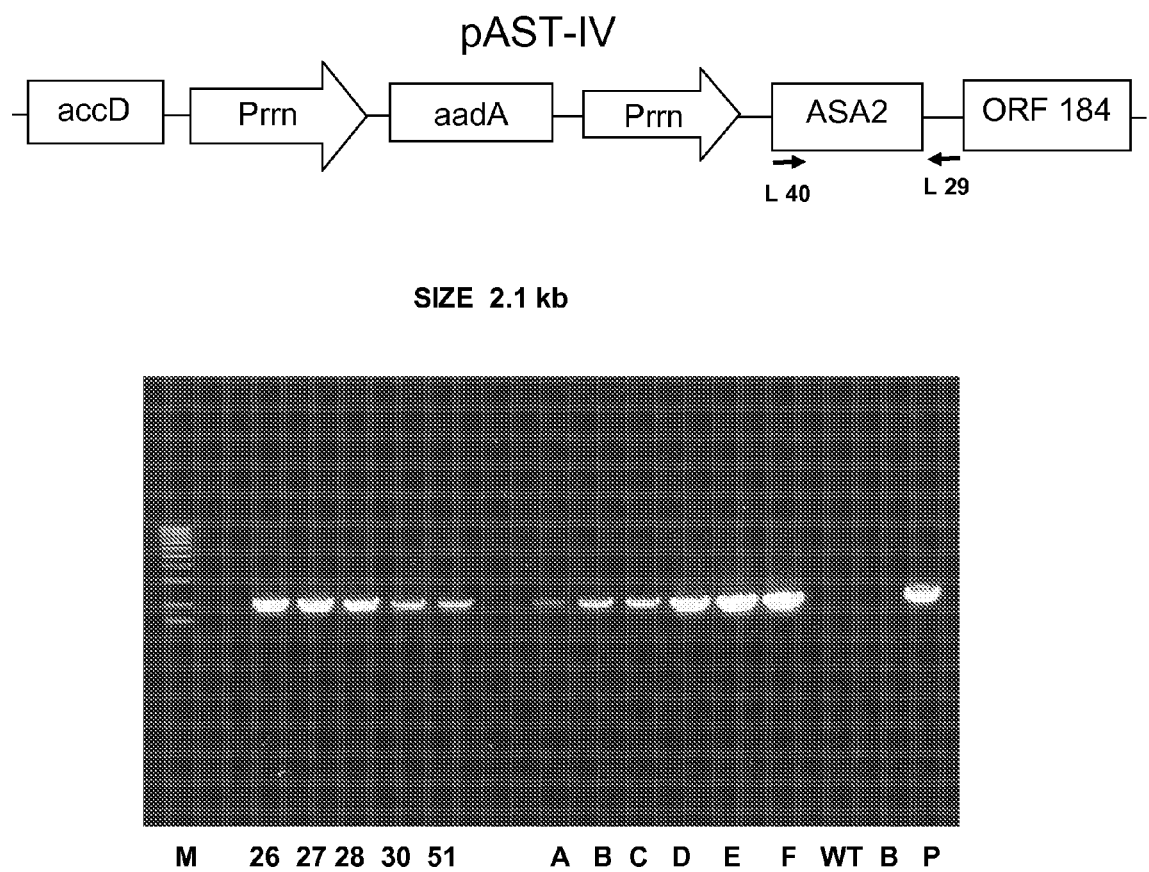
FIG. 6 shows PCR amplification with primers L29 and L40. M:DNA marker; 26-F: transgenic lines; WT: wild type cv. Havana; P: p-ASTIV plasmid; B: blank control. L29: located upstream of the plastid gene ORF184 (62343-62320).
Figure 13:
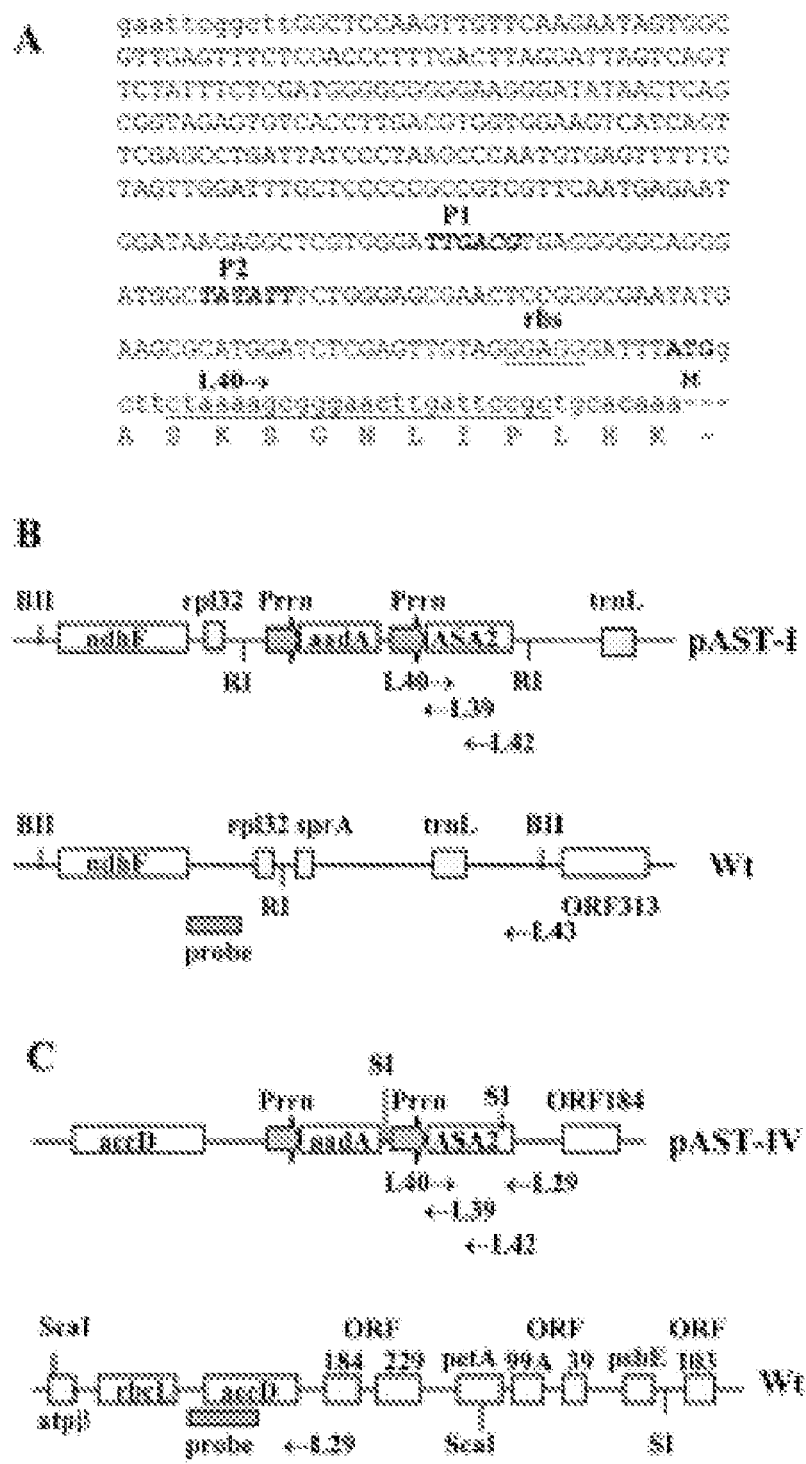
FIG. 13 shows structures of the plastid transformation vectors pAST-I and pAST-IV. A, Sequence of the modified plastid 16S rRNA operon promoter (Prrn) with a ribosomal-binding site (rbs) fused to a translation start codon ATG to initiate the coding region of the mature AS-subunit gene (ASA2). P1 and P2 (bold) are transcription regulatory sequences similar to the prokaryotic 30/10 upstream promoter elements. Only the first 13 amino acids of the predicted ASA2 protein sequence are shown. The location and direction of primer L40 is underlined (DNA: SEQ ID NO: 10 encodes PRT: SEQ ID NO: 11). B and C, Schematic structures of pAST-I, pAST-IV, and their corresponding regions of the wild-type tobacco plastid genome. The restriction enzymes reported are mapped. RI, EcoRI; BII, BglII; and SI, SacI. Also shown are the positions and directions of primers used and the location of the DNA fragments (thick black line) as probes for Southern hybridizations. The figure size is not to scale.
Figure 15:
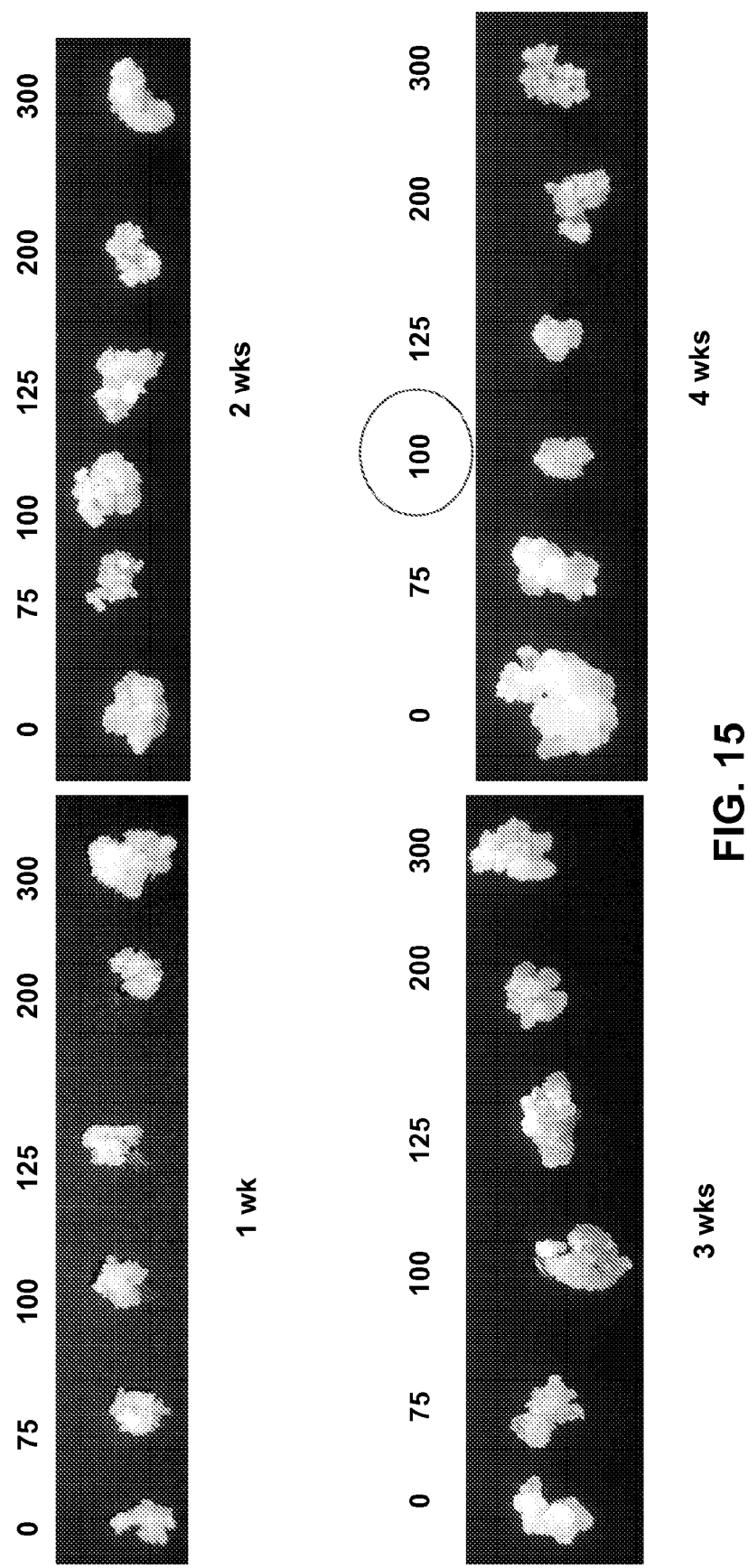
FIG. 15 shows 4MI $2^{nd}$ round of selection for Hi II cultivar.
Figure 16:
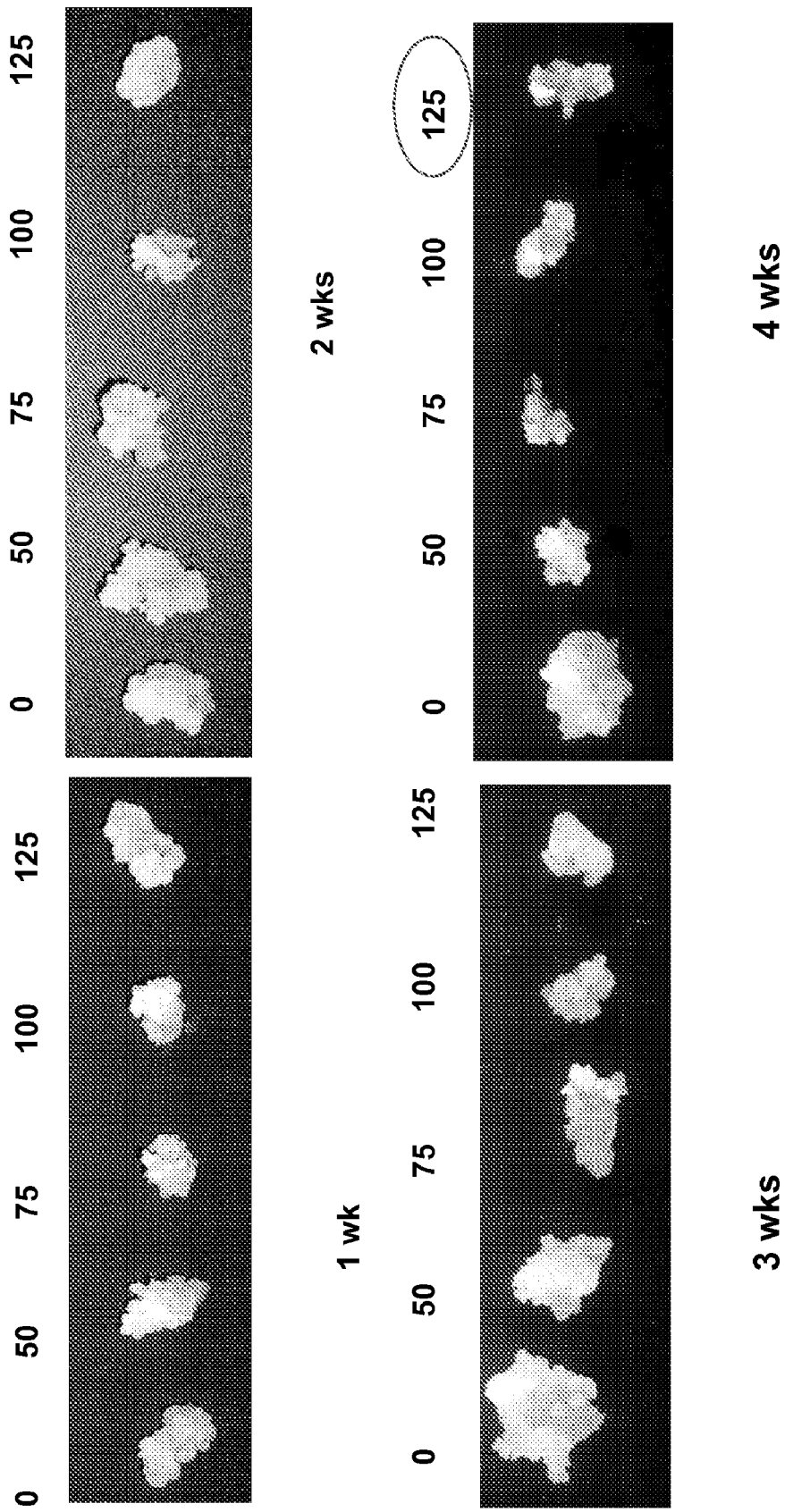
FIG. 16 shows 4MT $2^{nd}$ round of selection for Hi II cultivar.
Figures 17, 18:
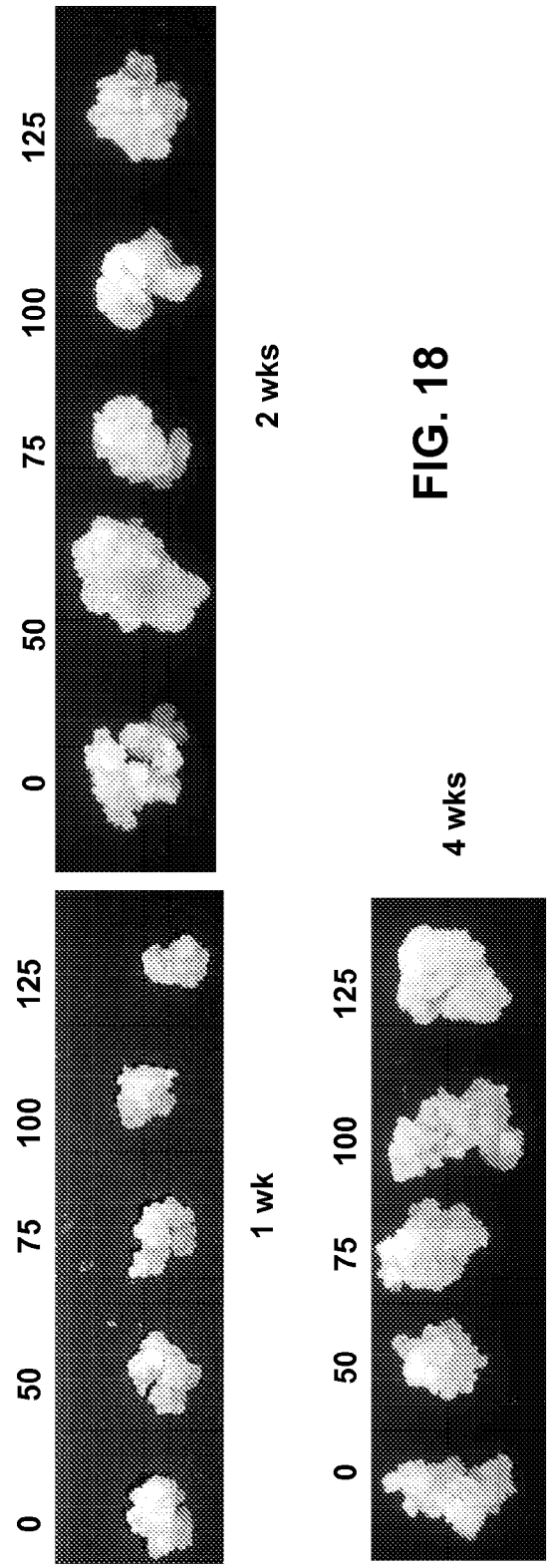
FIG. 17 shows concentration ranges of 4MI, 4MT and 5MI analogs in the $2^{nd}$ round screening.
FIG. 18 shows 5MI $2^{nd}$ round of selection for Hi II cultivar.
Figure 19:
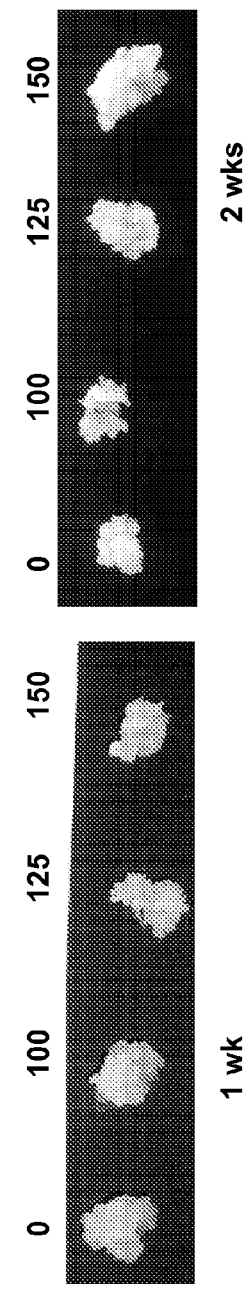
FIG. 19 shows concentration ranges of 4MI, 4MT, 5MI and 5MT analogs in the $2^{nd}$ round screening.
Figure 20:
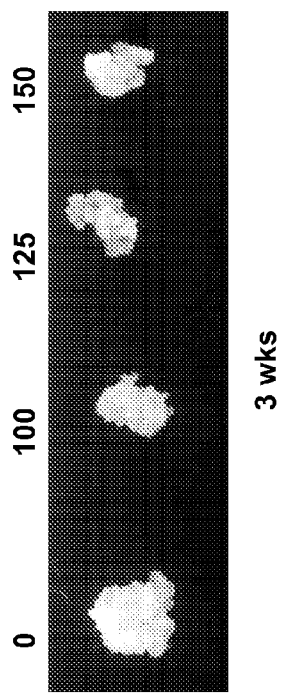
FIG. 20 shows 5MT $2^{nd}$ round of selection for Hi II cultivar.
Figure 21:
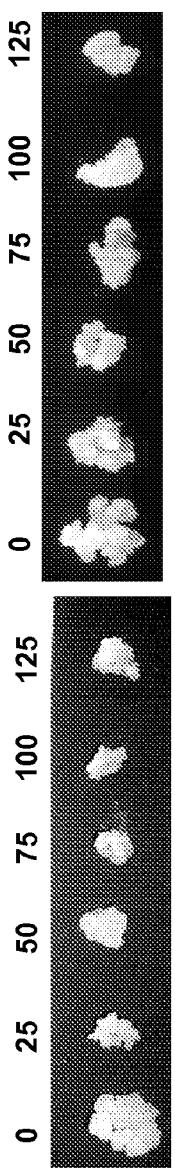
FIG. 21 shows concentration ranges of 4MI, 4MT, 5MI, 5MT and 7MT analogs in the $2^{nd}$ round screening.
Figure 22:
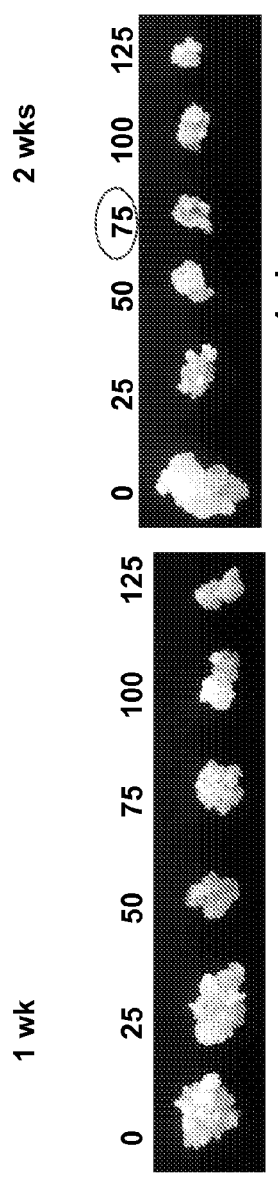
FIG. 22 shows 7MT $2^{nd}$ round of selection for Hi II cultivar.
Figure 23:
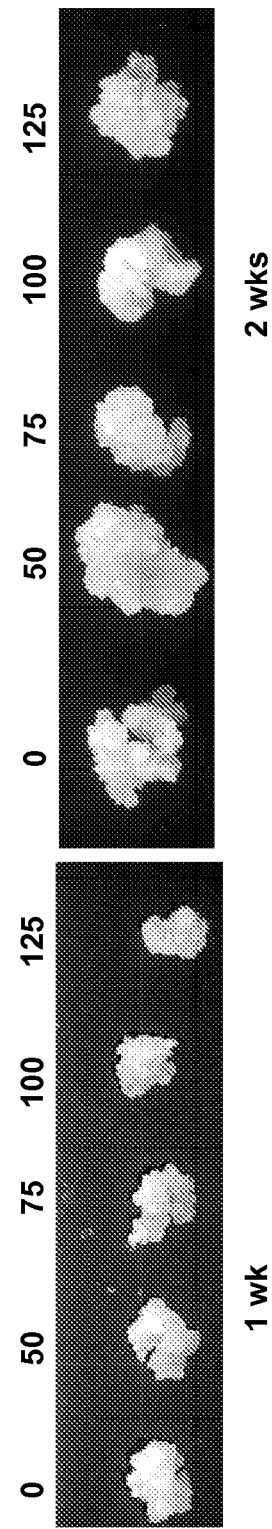
FIG. 23 shows concentration ranges of 4MI, 4MT, and 5MI analogs in the $2^{nd}$ round screening.
Figure 24:
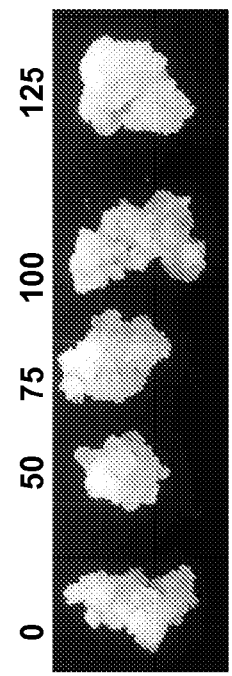
Figure 25:
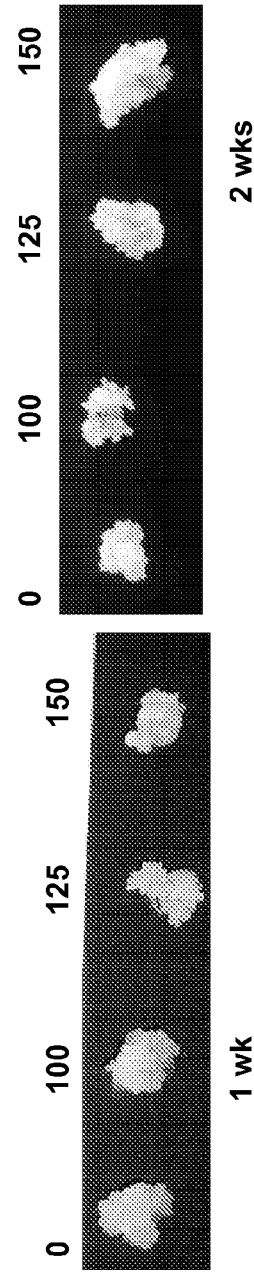
FIG. 25 shows concentration ranges of 4MI, 4MT, 5MI and 5MT analogs in the $2^{nd}$ round screening.
Figure 26:
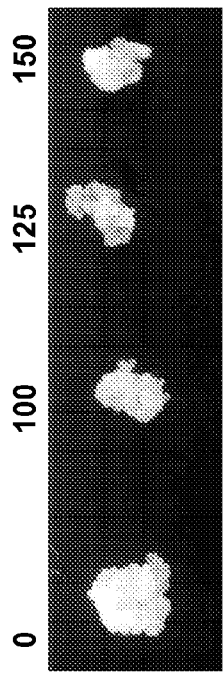
FIG. 26 shows 5MT $2^{nd}$ round of selection for Hi II cultivar.
Figure 27:
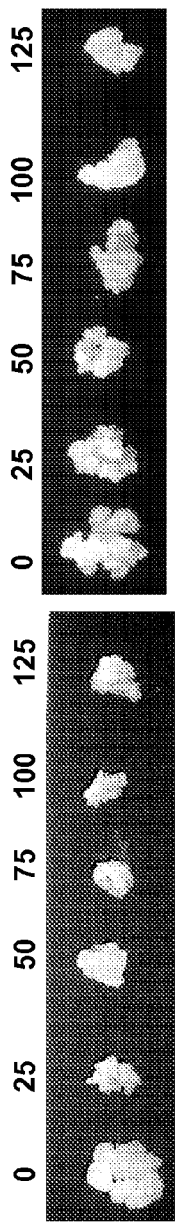
FIG. 27 shows concentration ranges used for various analogs in the $2^{nd}$ round screening.
Figure 28:
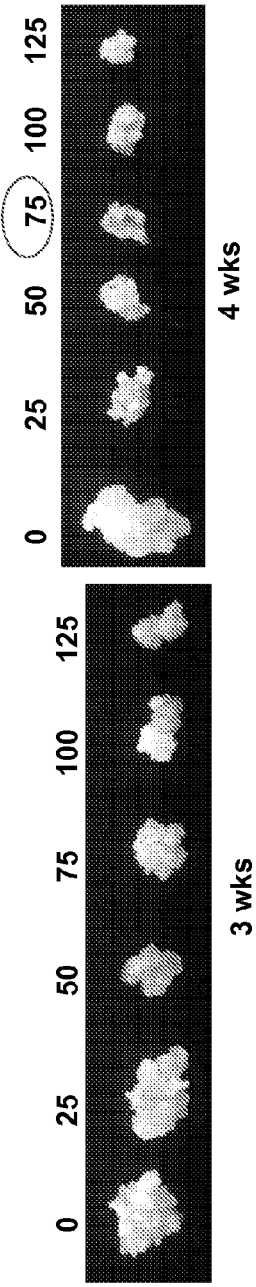
FIG. 28 shows 7MT $2^{nd}$ round of selection for Hi II cultivar.
Figure 29:
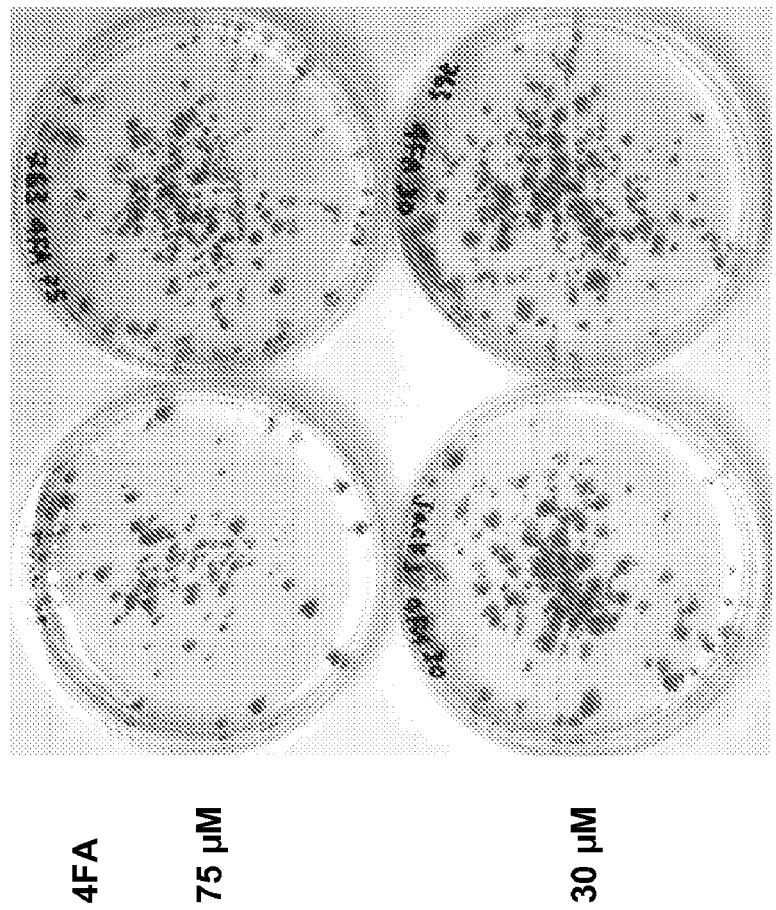
FIG. 29 shows a soybean embryogenic culture growth test with Trp analog 4FA.
Figure 30:
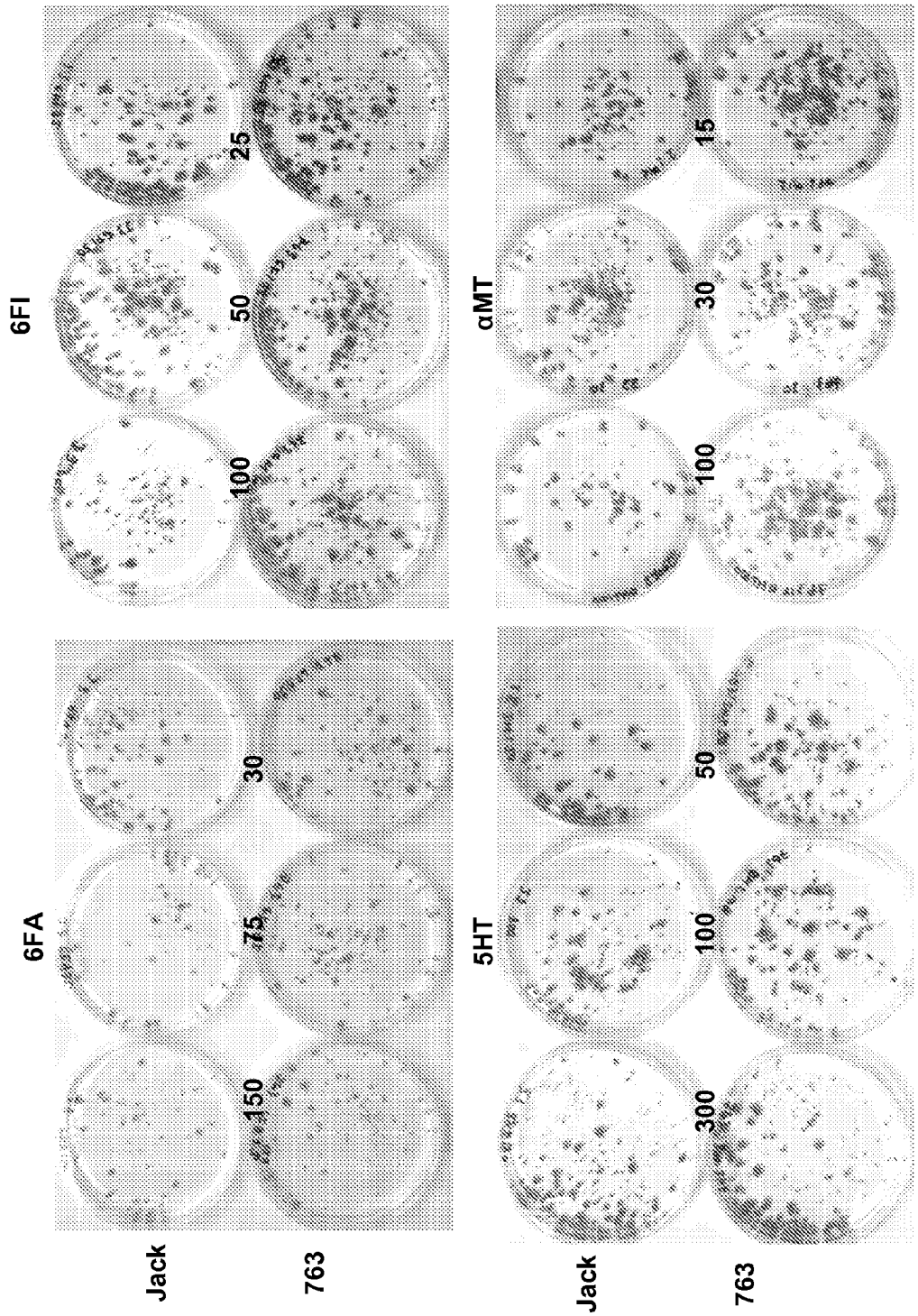
FIG. 30 shows a soybean embryogenic culture growth test with Trp or Indole analogs 6FA, 6FI, 5HT or 5MT.
Figure 32:
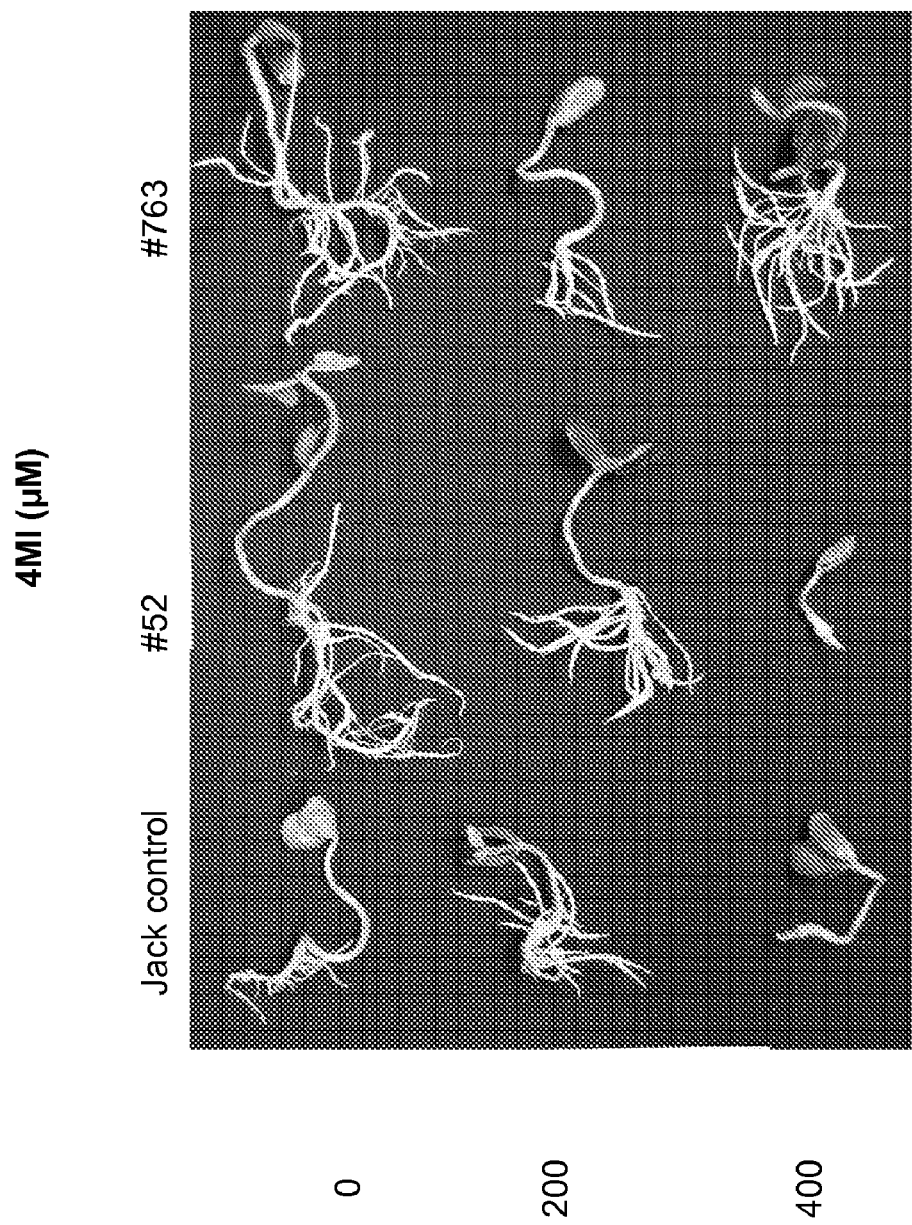
FIG. 32 shows soybean seed germination after 8 days in Trp analog 4MI.
Figure 33:
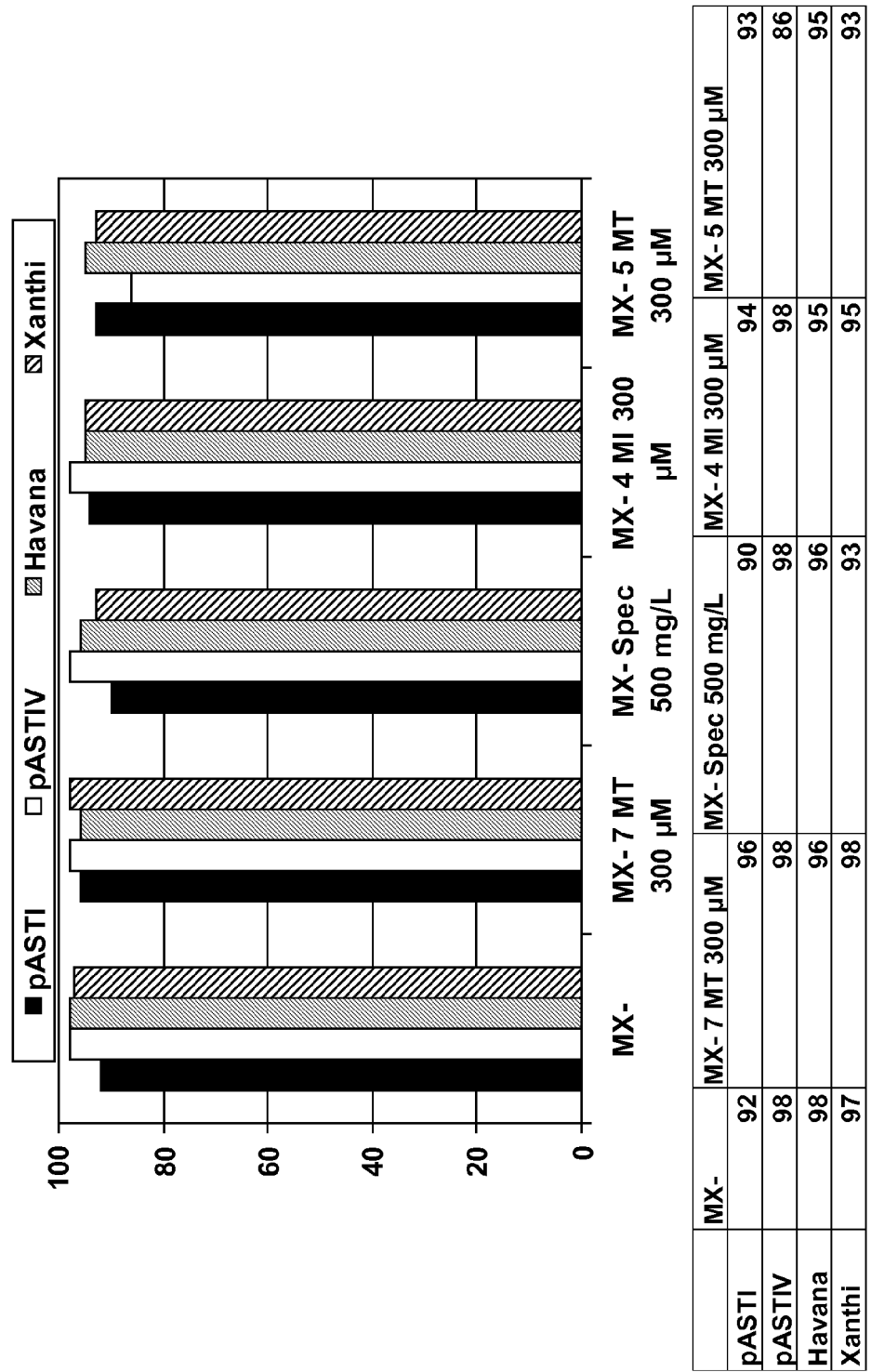
FIG. 33 shows growth inhibition test (GIT) second screening of 7MT and 4MI for tobacco seedling germination after 2 weeks.
Figure 34:
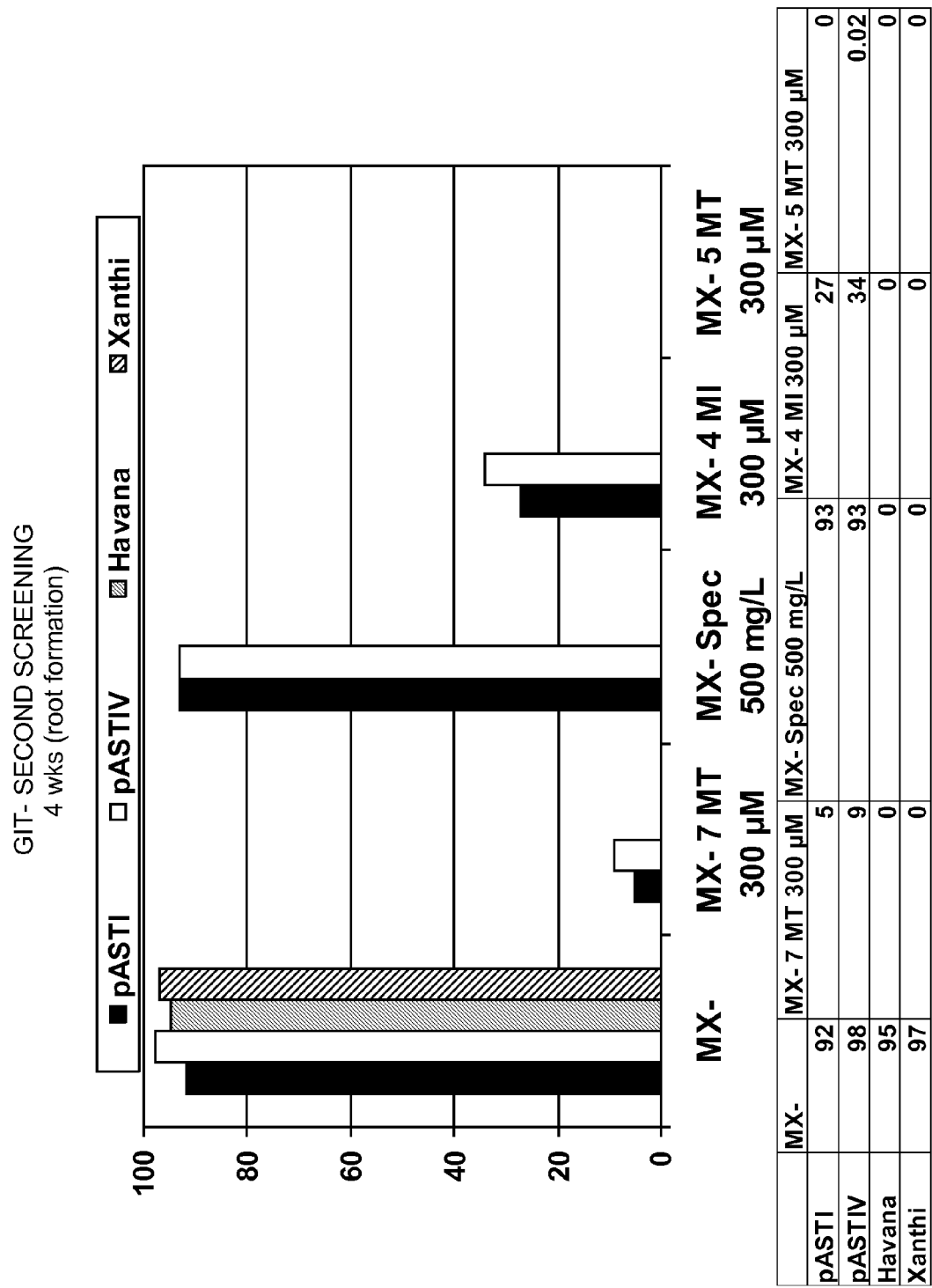
FIG. 34 shows growth inhibition test (GIT) second screening of 7MT and 4MI for tobacco root formation after 4 weeks.
Figure 35:
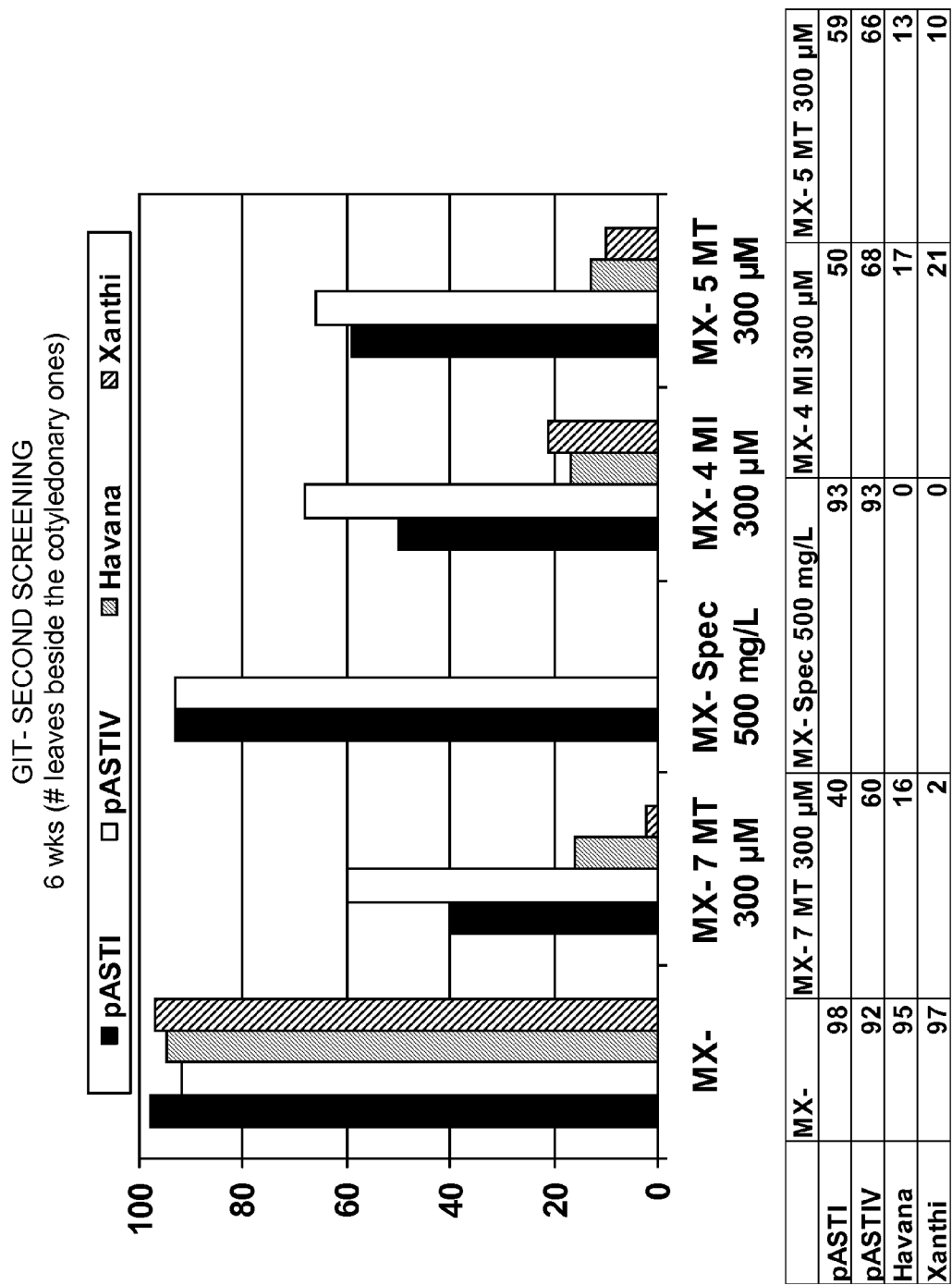
FIG. 35 shows growth inhibition test (GIT) second screening of 7MT and 4MI for tobacco leaf formation after 6 weeks.
Figure 36:
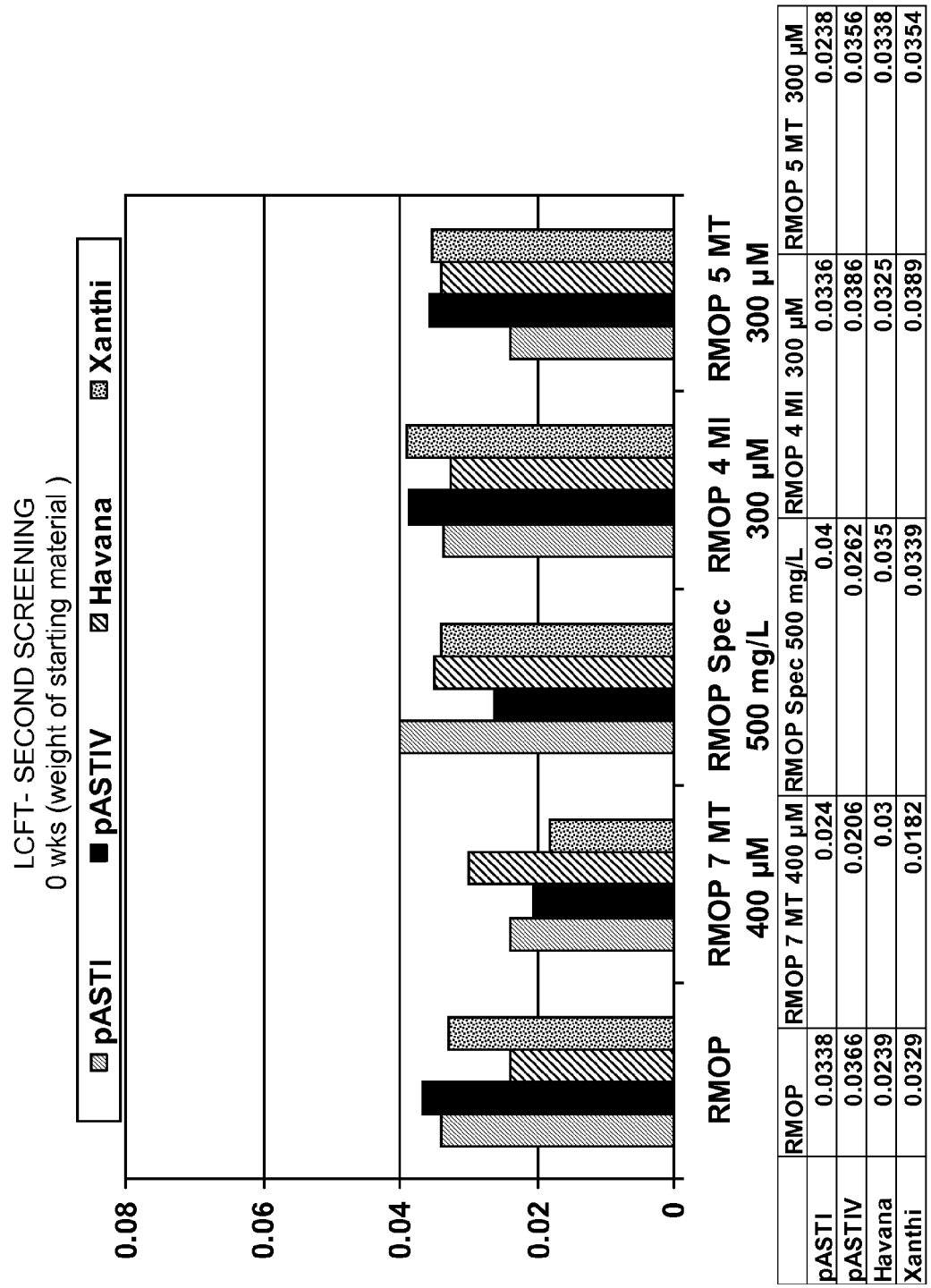
FIG. 36 shows leaf callus formation test (LCFT) at 0 wks (weight of starting material) of tobacco callus for 7MT and 4MI.
Figure 37:
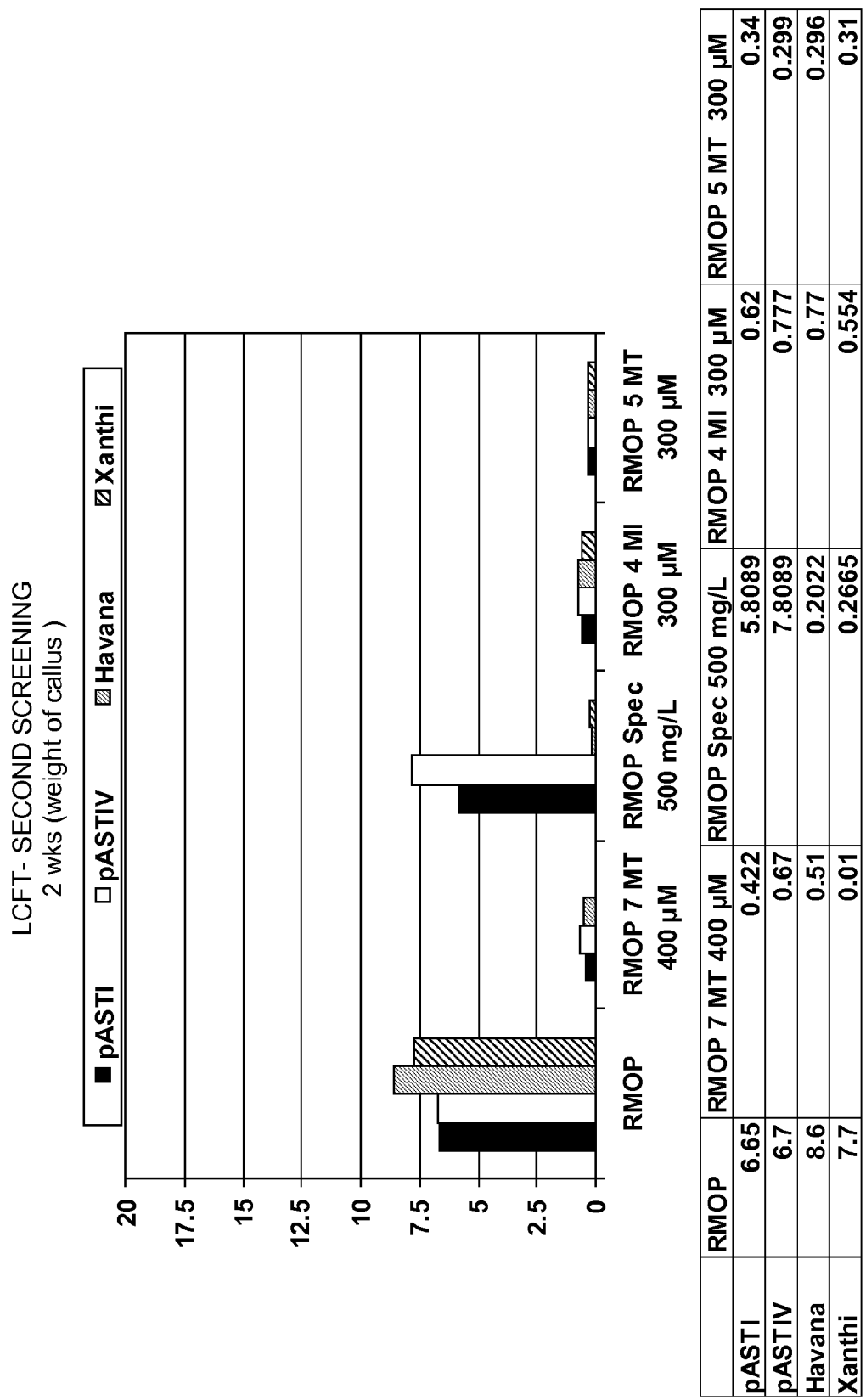
FIG. 37 shows LCFT second screening at 2 weeks (weight of callus).
Figure 38:
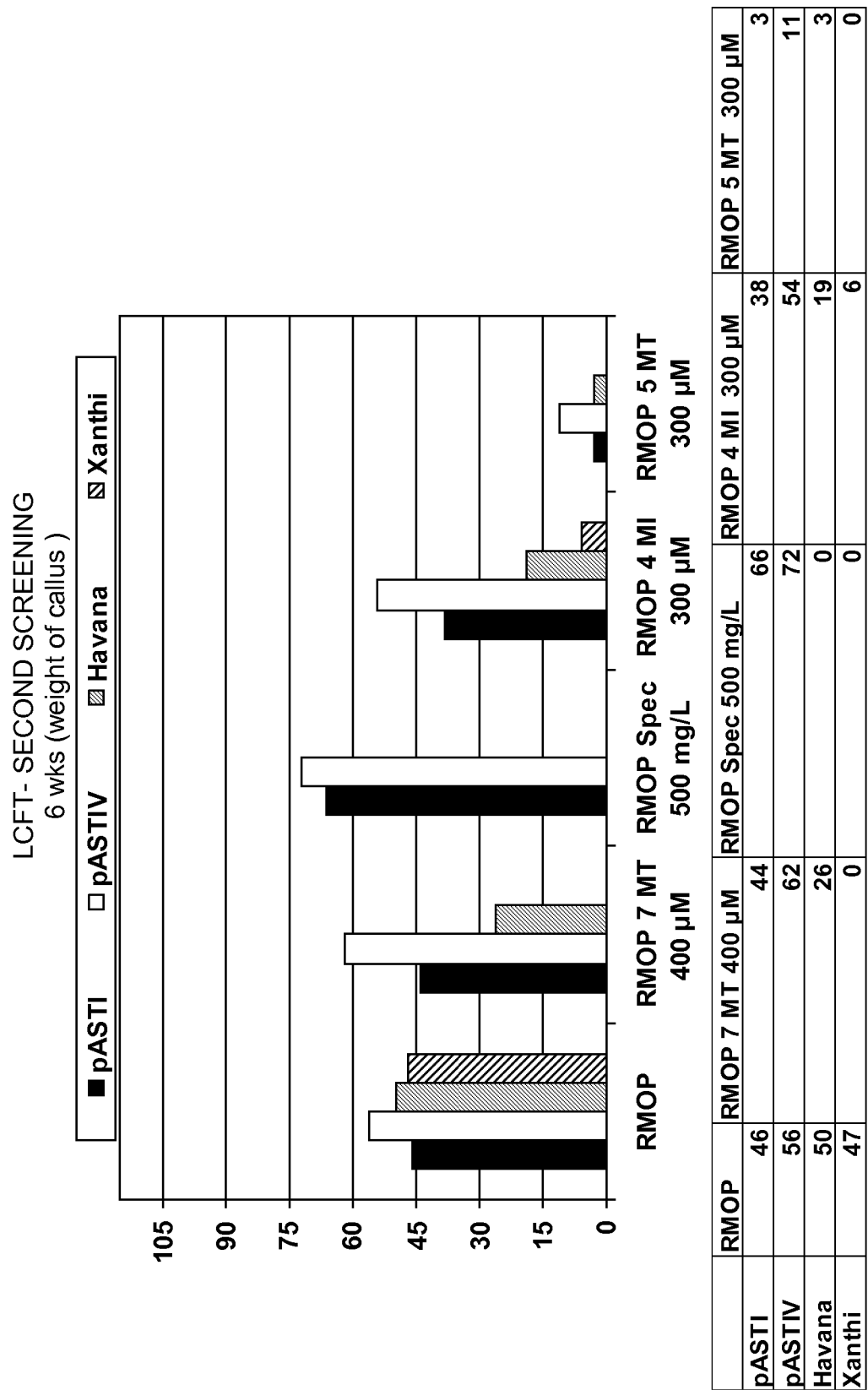
FIG. 38 shows LCFT second screening at 6 weeks (weight of callus).

Six to eight weeks after bombardment, 28 independent resistant shoots/calli were recovered from 60 leaf discs bombarded with vector pAST-IV. The 28 lines selected directly for 4MI or 7MT resistance were tested by the PCR reaction using either primers specific for ASA2 gene (L40 and L 39) or a primer specific to the ASA2 coding region (L40) and a primer that is located in the plastid genome outside the flanking region of the vector (L29). The controls were the wild-type *N. Tabacum* cv. Havana and the amplified 815 bp (L40-L39) or the 2.1 kb (L40-L29) fragments from the vector pAST4V (FIG. 13). A 815 bp (L40-L39) and a 2.1 kb (L40-L29) fragments were reproducibly detected in 5 transgenic of the 28 in dependent lines (3 from 7MT and 2 from 4 MI). (FIGS. 5 and 6). FIG. 7 shows northern-blot hybridization was carried out to determine the expression of the Prrn-ASA2 gene in the transformed plants.

Example 4

Nucleic Acid Analysis of Transformed Plants

Genomic DNA was isolated from young fully expanded leaves using the a CTAB extraction method. Alternatively, total cellular DNA and RNA can be extracted using Qiagen Kits (Qiagen, Valencia, Calif.). Restriction endonuclease treatment of 8 µg DNA per sample was performed using 5 units/µg of Sca I enzyme in an appropriate buffer, at 37° C. for 5 h. The treated DNA was separated by 0.8% agarose gel electrophoresis in TAE buffer and then blotted onto a nylon membrane (Hybond-N+, Amersham) and cross linked to the membrane by UV. The accD probe was prepared by PCR using primers designed to amplify a 1.2 kb fragment. The probe was radiolabeled with $\alpha$-32P-labeled dCTP (3,000 Ci/mmol) through the random primer method Megaprime (Amersham Biosciences). Prehybridization, hybridization and subsequent washing steps were performed according to standard protocols. Signals were detected by exposing the blots to autoradiography films (Biomax, Kodak,) for 1-5 days at −70° C. depending on the intensity of the blots.

The Southern blot hybridization analyzed the DNA samples isolated from the 5 transgenic lines and WT control. The hybridization of Sca I digestion results in an 8,933 bp fragment containing accD to petA gene in the wild type plant but generates a 12.4 kb band in the transgenic lines due to the insertion of the 3.5 kb expression cassette (FIG. 8). T

Example 5

RT-PCR Analysis of Transformed Plants

RT-PCR (Reverse Transcription-Polymerase Chain Reaction) was used to detect the expression of the ASA2 gene. Total RNA was isolated using the RNeasy Plant Mini Kit from young fully expanded leaves from both transgenic lines and wild type (WT). Total RNA was then treated with rDNase I to eliminate any genomic DNA contamination.

The primers used for the one-step reaction were the same as the ones used for the PCR screening (L40-L39). The fragment amplified was 815 bp long and a PCR reaction on Total RNA rDNase treated was performed with the same primers without the Reverse Transcriptase step (Reverse Transcription and Initial Denature below) to demonstrate the absence of genomic DNA contamination in the samples. The cycling conditions were:

| Reverse Transcription | 42° C. | 30 minutes |
|---|---|---|
| Initial Denature | 94° C. | 2 minutes |
| Denature | 94° C. | 30 seconds |
| Anneal | 155° C. | 30 seconds |
| Extension | 68° C. | 30 seconds |
| Repeat previous 3 cycles 30 times | | |
| Final Extension | 68° C. | 5 minutes |

Figure 9:
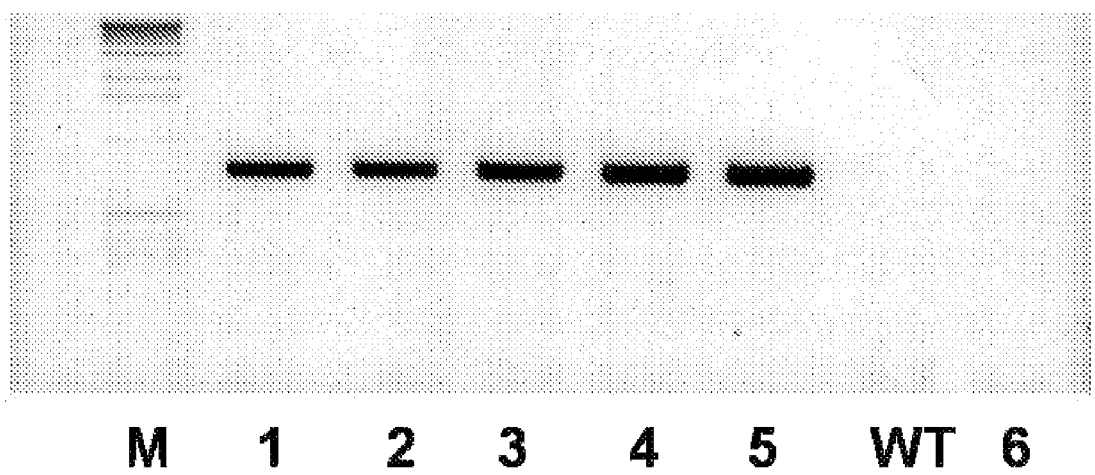
FIG. 9 shows RT-PCR on total RNA rDNase treated. M: 1 Kb DNA ladder lanes 1-5: transgenic plants; WT: wild type cv. Havana; lane 6: blank control.
Figure 10:
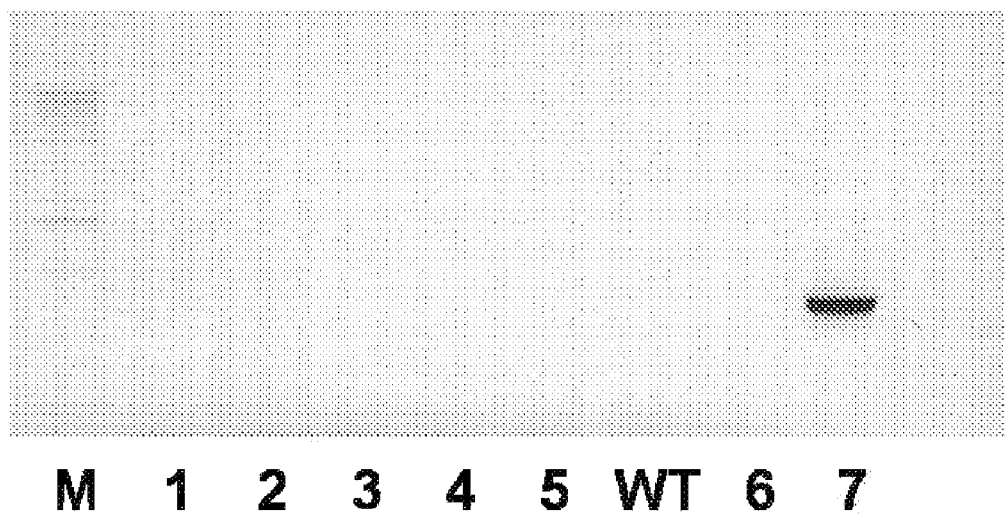
FIG. 10 shows PCR amplification with ASA2 specific primers L39 and L40 using as template total RNA rDNase treated. M: DNA marker; 1-5:transgenic lines; WT: wild type cv. Havana; lane 6: blank control lane 7: p-ASTIV plasmid.

FIG. 9 shows that an 815-bp fragment was amplified by RT-PCR from total RNA extracted from young leaves in the five transgenic lines while no fragment was detected in the WT. Therefore, the naturally occurring ASA2 gene appears to be expressed at a very low level. FIG. 10 shows the control reaction using total RNA as template without the Reverse Transcriptase Reaction. As expected only the plasmid pASTIV gave a PCR product. The total RNA was free from any genomic DNA contamination

Example 6

Analysis of AS Enzyme Activity

Approximately 2 g of leaves was homogenized with 1.5 volume of ice-cold extraction buffer as described in Bernasconi et al., (1994). The homogenate was centrifuged at 30,000 g at 4° C. for 10 min. The supernatant was desalted using a Econo-Pac 10 DG column (Bio-Rad, Hercules, Calif.). Protein concentration was determined using a protein dye-binding assay kit (Bio-Rad, Hercules, Calif.). The supernatant was combined with two volumes of assay buffer as described previously (Bernasconi et al., 1994) but without $NH_4Cl$. AS enzyme activity was measured as the conversion rate of chorismate to anthranilate as described previously (Song et al., 1998). Either 100 mM NH4Cl or 10 mM glutamine was added to the assay mixture to determine $\alpha$-subunit activity or AS holoenzyme activity respectively and Trp at different concentrations. Duplicate extracts of each line were analyzed.

Figure 11:
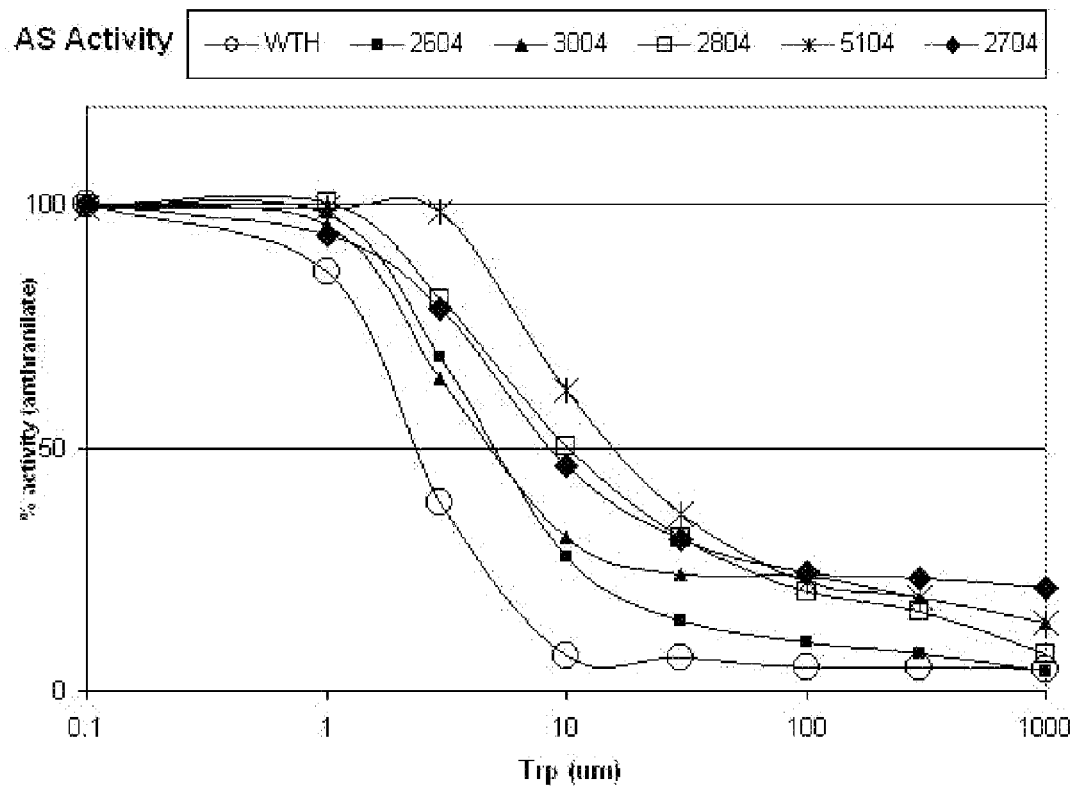
FIGS. 11 and 12 graphically present the inhibition by Trp of AS activity in untransformed line, wild-type (WT) and the 5 transgenic lines produced via plastid transformation. Relative activity is the percentage of the activity with no Trp added. Holoenzyme activity measured with 10 mM Gln as the amino donor (FIG. 11). AS α subunit activity measured with 100 mM $NH_4Cl$ as the amino donor (FIG. 12).
Figure 12:
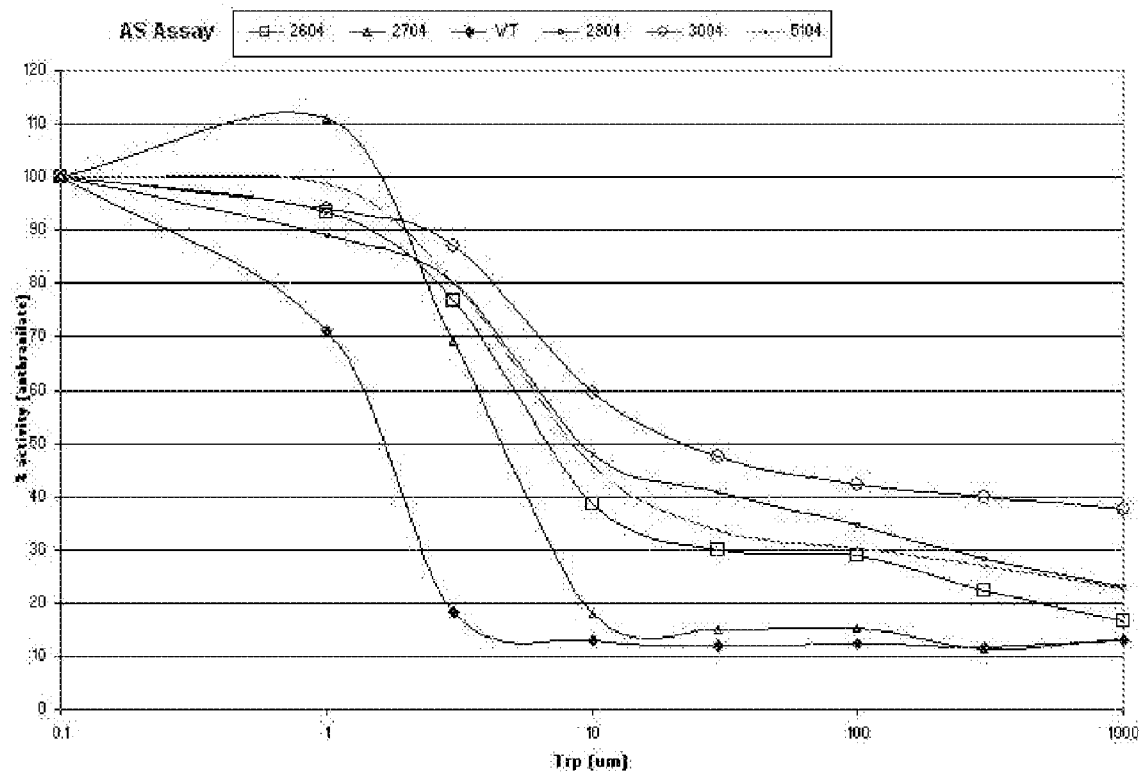

Either with 10 mM glutamine (FIG. 11) or 100 mM $NH_4Cl$ (FIG. 12) as amino donor in all the five transgenic lines tested AS was less sensitive to Trp inhibition than AS from the WT (FIG. 11). Either for the Holoenzyme activity (FIG. 11) or the $\alpha$ subunit activity (FIG. 12) at 10 µm the WT AS activity was almost completely inhibited while the transgenic lines AS still retained from 20 to 60% of the activity.

Example 7

Free Trp Analysis of Transformed Plants

Young expanded leaves of each of the transgenic tobacco lines produced were analyzed for free Trp content. Free Trp was extracted with 0.1 N HCl as previously described previously (Cho et al., 2000). Trp concentration was measured by HPLC. Free tryptophan data are shown in FIGS. 39-40 for several transgenic lines of tobacco as compared to the wild type.

Example 8

Growth Inhibition of Various Trp, Indole and Anthranilate Analogs in Various Plant Species Maize callus was tested for the biolistic plastid transformation. The immature embryos used for the induction were obtained from the maize line C28 previously selected for resistance on 5MT (U.S. Pat. No. 4,642,411) and from line Hi II. Callus pieces are placed on solid medium with different concentrations of the different analogs to test the feasibility of using them for the direct selection of transformants after bombardment with the ASA2 vector (see FIGS. 15-28:).

Various concentrations of the different analogs were tested on maize, soy bean, and tobacco that includes growth inhibition test of germination, leaf callus formation test, and other growth inhibition tests (FIGS. 15-38).

TABLE 2

Trp, Indole and Anthranilate analogs for discriminating between wild type and ASA2 expressing *Arabidopsis* germinating seedlings and tobacco shoot producing leaf discs. The concentrations are indicated in μM.

| *Arabidopsis* seeds | Tobacco leaf discs |
|---|---|
| α-MT 20 μM | 4MI 300 |
| 5MT 200 | 5MI 1000 |
| 4MT 70 | 7MI 1000 |
| 5HT 200 | 3-acetylI 500 |
| 7MT 300 | 7MT 400 |
| 4FI 70 | 5FA 150 |
| 5FI 20 | 5MA 800 |
|  | 6MA 70 |

TABLE 3

Trp, Indole and Anthranilate analogs for discriminating between wild type and ASA2 expressing *Arabidopsis* germinating seedlings and tobacco shoot producing leaf discs

| *Arabidopsis* Tested | Tobacco Tested |
|---|---|
| Trp analogs | |
| α-MT, 5FT, 6FT, 7azaT, 4FT, 5hydroxyT, 7MT, 5MT, 4MT | same as *Arabidopsis* and also 6MT was tested |
| Indole analogs | |
| 4FI, 5FI, 7MI, 5aminoI, 7azaI, 6methoxyI, 3acetylI, 5hydroxyI, 3aminoI, 4aminoI, 5MI | same as *Arabidopsis*, 6-methoxyI and 3-aminoI not tested. |
| Anthranilate analogs | |
| For example, 2-amino-4-flurobenzoic acid = 4FA since 2-aminobenzoic acid is anthranilic acid. | |
| 6FA, 5-chlorA, 4-chloroA, 3-hydroxyA, 3MA, 5MA, 6MA | same as *Arabidopsis*, and 4FA, 5FA and 5iodoA were tested, and 4-chloroA was not tested. |

Example 9

Analysis of ASA2 Transformed Plants Under the Control of a CaMV35S Promoter

A vector pC2ASA2 was used, which contains a full length 2,144-bp AS feedback-insensitive α-subunit (ASA2) cDNA, encoding 616 amino acids including a putative transit peptide and 204 bp of 3'non-coding region driven by the CaMV35S promoter. pC2ASA2 was electroporated into *Agrobacterium tumefaciens* strain EHA105 and then used for the leaf disc transformation. Shoots of tobacco (*Nicotiana tabacum* L. cv. Xanthi) plants were maintained as in vitro stock cultures in Magenta boxes containing MS basal medium (Murashige and Skoog 1962) with 2 g 1-1 Gelrite® and leaves from these shoots were sources of explants for transformation. The growth conditions were 16-h photoperiod with a temperature of 28° C., florescent lamps providing a photosynthetic photon flux density of 150 μmol m-2 s-1 at the shelf surface. For segregation tests or for seedling growth inhibition tests on different analogs, 50 seeds/plate were surface sterilized with a solution of distilled water-Clorox (80:20; 1.25% Na hypochlorite) for 20 min containing a few drops of Tween 20™ and then rinsed with sterile water before spreading them on MS basal medium plates containing the appropriate selective agent.

Leaf callus/shoot formation was studied on Tobacco Regeneration Medium that was MS basal medium with 88 μM 6-benzyladenine (BA) and 0.5 μM naphthalene acetic acid (NAA) and various concentrations of different Trp and indole analogs using a total of 30 leaf discs (6 mm each in diameter) from either the untransformed wild type (WT) tobacco or the ASA2 expressing transgenic line transformed with pAST-IV vector (line ASTIV) at 28° C. under fluorescent light as described above. Callus formation and shoot production was visually evaluated after 2, 4 and 6 weeks. Seedling growth inhibition was studied as described herein.

Leaf discs (6 mm each in diameter) from 20 leaves of WT tobacco were used for each transformation experiment. After 6 weeks of selection on TRM with either 300 μM 4MI or 300 μM 7MT and 500 mg/l timentin to eliminate *A. tumefaciens*, the shoots regenerating from the callus were isolated and transferred to the Rooting Medium with analogs to initiate root growth. After root induction, the plantlets were transferred into soil and grown to maturity in a greenhouse. The T1 seeds were plated on either 4MI or 7MT for segregation tests and to obtain homozygous lines.

PCR was carried out to identify the insertion of the ASA2 and GUS genes. Taq DNA polymerase (New England Biolabs Inc., Ipswich, Mass.) was used for 30 cycles at 94° C. for 45 s, 55° C. for 45 s and 72° C. for 1.3 min. The primers used for amplification of a 815 by fragment of the ASA2 gene were ASAF 5'-CTA AAA GCG GGA ACT TGA TTC CGC-3' (SEQ ID NO: 1) located at the beginning of the mature ASA2 coding region and ASAR 5'-TCT GTA CAC TTC AAA TGG GTC AGC-3' (SEQ ID NO: 2) located in the middle of the ASA2 coding region while for the amplification of a 1.3 kb fragment of the GUS gene were GusintF 5'-GGT ATC AGC GCG AAG TCT TT-3' (SEQ ID NO: 5) and GusintR 5'-TCG GTG ATG ATA ATC GGC TG-3' (SEQ ID NO: 6)

For Southern hybridization analysis restriction endonuclease treatment of 5 μg DNA per sample was performed using 5 units/μg of BamHI (New England Biolabs Inc., Ipswich, Mass.) enzyme in the manufacturer's buffer, at 37° C. for 5 h. The treated DNA was separated by 0.8% agarose gel electrophoresis in TAE buffer 1× and then blotted onto a nylon membrane (Hybond-N+, GE Healthcare Limited, Little Chalfont, UK) and cross linked to the membrane by UV. The ASA2 probe was prepared by PCR using primers designed to amplify a 0.8 kb fragment (ASAF-ASAR). The probe was radiolabeled with α-32P-labeled dCTP (3,000 Ci/mmol) through the random primer method Megaprime (GE Healthcare Limited). Prehybridization, hybridization and subsequent washing steps were performed according to standard protocols. Signals were detected by exposing the blots to autoradiography films (Denville Scientific Inc., NJ) for 1-5 days at −70° C. depending on the intensity of the blots.

Total RNA was extracted from young expanded leaves with RNeasy kits (Qiagen, Valencia, Calif.) and treated with rDNase I RNase-Free (USB Biochemicals, Cleveland, Ohio) to eliminate any genomic DNA contamination. RT-PCR (reverse transcription-polymerase chain reaction) was used to detect the expression of the ASA2 gene. The primers used for the one-step reaction were the same as the ones used for the PCR screening (ASA2F-ASA2R). The fragment amplified was 815 bp long and a PCR reaction on total RNA rDNase I RNase-Free treated was performed with the same primers without the reverse transcriptase step to demonstrate the absence of genomic DNA contamination in the samples. A 210 by fragment of the 18S gene was amplified using primers 18S Rev 5'-TAAGAACGGCCATGCACCACC-3' (SEQ ID NO: 7) and 18S For 5'-AAGGAATTGACGGAAGGGCACCA-3' (SEQ ID NO: 8) to act as internal control.

Among the 9 Trp analogs and 7 indole analogs tested the most effective were 7MT and 4MI. At 300 µm 4MI and 300 µm 7MT, the callus production of the WT was inhibited and the leaf discs turned brown with little shoot formation. However the ASA2 expressing leaf discs formed callus and produced shoots after four/six weeks.

Seedling Growth Inhibition Test with 4MI and 7MT: When placed on analog containing medium both WT and ASTIV seeds could germinate almost equally on medium with either 75 µm 4MI or 75 µm 7MT but after two weeks WT seedlings started to bleach, ceased to grow and eventually died. In contrast transgenic seedlings grew well on the same concentration of 4MI or 7MT. After six weeks the transgenic seedlings were growing with normal true leaf development. Generation and selection of transgenic plants on 4MI or 7MT.

The ASA2 gene driven by the CaMV 35S promoter was transferred into tobacco leaf discs via the *A. tumefaciens*-mediated transformation method. Putative transformants were selected on TRM using the optimal concentration (300 µm) of 4MI and 7MT for selection. 31 resistant plants were obtained in two different experiments: 21 one on 4MI from a total of 150 leaf discs (10 resistant plants from 80 leaf discs in experiment 1 and 11 resistant plants from 70 leaf discs in experiment 2) and 10 on 7MT from a total of 135 leaf discs (6 resistant plants from 70 leaf discs in experiment 1 and 4 resistant plants from 65 leaf discs in experiment 2). All transgenic lines, once confirmed by genomic PCR for the ASA2 and GUS genes were rooted on rooting medium with the respective analog. Southern analysis showed that the transgenic lines contain ASA2 hybridizing fragments and usually only one copy of the transgene. GUS activity was assessed histochemically in PCR-GUS positive lines using leaf pieces confirming the results obtained with the molecular screening. When the transgenic plants were tested for ASA2 gene expression by RT-PCR an 815-bp fragment was amplified from total RNA extracted from young leaves from 15 transgenic lines while no fragment was detected in the WT. Therefore the naturally occurring ASA2 gene appears to be either expressed at very low level or not at all in tobacco leaves. A control reaction using total RNA as template without the reverse transcriptase reaction was also carried out. As expected only the plasmid pC2ASA2 gave a PCR product. Hence the total RNA used was free from any genomic DNA contamination. The 18 S gene was used as a control to normalize for sample to sample variations in total RNA amounts and for reaction efficiency to normalize for sample to sample variations in total RNA amounts and for reaction efficiency.

To test for the segregation of the transgene in the T1 generation, seeds of the transgenic lines were germinated on medium containing either 75 4MI or 75 µm 7MT for 21 days. The ratios of resistant/sensitive seedlings were for most of the lines close to the expected 3:1 ratio confirming a single nuclear site of insertion for the 15 lines tested. The seedlings growth test with T2 seed from four lines randomly selected from the fifteen resistant plants identified in the segregation test showed that they were all homozygous for the ASA2 gene since all 100 seeds germinated and grew normally on either 75 µm 4MI or 75 µm 7MT.

Tryptophan content and AS activity of the transgenic lines: Since the ASA2 enzyme is insensitive to feedback inhibition by Trp the free Trp levels in the TO transgenic plant leaves were measured. Line #7 selected on 300 µM 4MI contained 8 times as much free Trp as did the WT (276 nmol g-1 FW and 45 nmol g-1 FW, respectively) and the other ASA2 transgenic lines accumulated less free Trp than line #7 ranging from 2 to 5 times more then WT.

Of the 15 transgenic lines tested for AS activity, two lines (line #6 and line #7) showed holoenzyme and α-subunit activity much less sensitive to Trp inhibition than that of the WT. At 300 µM Trp the WT relative holoenzyme activity is almost completely inhibited whereas line #6 and line #7 still retained about 40% of the total activity. The specific activity of the holoenzyme with no Trp added for the control WT was 20.5 pmol min-1 mg-1 protein and 90.0 and 105.9 pmol min-1 mg-1 protein for line #6 and line #7, respectively. When the α-subunit activity was measured lines #6 and line#7 lines still retained about 40% of the total activity with 300 µM Trp. The specific activity of the holoenzyme with no Trp added for the control WT was 29.9 pmol min-1 mg-1 protein and 38.5 and 118.2 pmol min-1 mg-1 protein for line #6 and line #7, respectively.

The coding sequence of the feedback insensitive ASA2 gene, designated by GenBank Accession No. AF079168 is disclosed herein.

```
                                            (SEQ ID NO: 9)
       a tgcagtcgtt acctatctca taccggttgt ttccggccac ccaccggaaa gttctgccat tcgccgtcat ttctagccgg agctcaactt ctgcacttgc gcttcgtgtc cgtacactac aatgccgctg ccttcactct tcatctctag ttatggatga ggacaggttc attgaagctt ctaaaagcgg gaacttgatt ccgctgcaca aaaccatttt ttctgatcat ctgactccgg tgctggctta ccggtgtttg gtgaaagaag acgaccgtga agctccaagc tttctctttg aatccgttga acctggtttt cgaggttcta gtgttggtcg ctacagcgtg gtgggggctc aaccatctat ggaaattgtg gctaaggaac acaatgtgac tatattggac caccacactg gaaaattgac ccagaagact gtccaagatc ccatgacgat tccgaggagt atttctgagg gatggaagcc cagactcatt gatgaacttc ctgataccct tgtggtgga tgggttggtt atttctcata tgacacagtt cggtatgtag agaacaggaa gttgccattc ctaagggctc cagaggatga ccggaacctt gcagatattc aattaggact atacgaagat gtcattgtgt ttgatcatgt tgagaagaaa gcacatgtga ttcactgggt gcagttggat cagtattcat ctcttcctga ggcatatctt gatgggaaga aacgcttgga aatattagtg tctagagtac aaggaattga gtctccaagg ttatctcccg gttctgtgga tttctgtact catgcttttg gaccttcatt aaccaaggga aacatgacaa gtgaggagta caagaatgct gtcttacaag caaaggagca cattgctgca ggagacatat ttcaaatcgt tttaagtcaa cgctttgaga gaagaacatt tgctgaccca tttgaagtgt acagagcatt aagaattgtg aatccaagcc catatatgac ttacatacaa gccagaggct gtattttagt tgcatcgagc ccagaaattt tgacacgtgt gaagaagaga agaattgtta
```

-continued

```
atcgaccact ggctgggaca agcagaagag ggaagacacc tgatgaggat gtgatgttgg aaatgcagat gttaaaagat gagaaacaac gcgcagagca catcatgctg gttgatttag gacgaaatga tgtaggaaag gtgtcaaaac ctggttctgt gaatgtcgaa aagctcatga gcgttgagcg gtattccat gtgatgcaca taagctccac ggtctctgga gagttgcttg atcatttaac ctgttgggat gcactacgtg ctgcattgcc tgttgggacc gtcagtggag caccaaaggt aaaggccatg gagttgattg atcagctaga agtagctcgg agagggcctt acagtggtgg gtttggaggc atttcctttt caggtgacat ggacatcgca ctagctctaa ggacgatggt attcctcaat ggagctcgtt atgacacaat gtattcatat acagatgcca gcaagcgtca ggaatgggtt gctcatctcc aatccggggc tggaattgtg gctgatagta atcctgatga ggaacagata gaatgcgaga ataaagtagc cggtctgtgc cgagccattg acttggccga gtcagctttt gtaaagggaa gacacaaacc gtcagtcaag ataaatggtt ctgtgccaaa tctattttca agggtacaac gtcaaacatc tgttatgtcg aaggacagag tacatgagaa aagaaactag
```

MX-Medium (Rooting)

| Ingredient | Add per 1 L |
| --- | --- |
| MS I | 100 ml |
| MS II | 10 ml |
| NaFeEDTA | 1 ml |
| MB+ | 10 ml |
| Sucrose | 30 g |
| Bring up to volume and then pH | |
| pH | 5.7~5.9 |
| Add Agar | |
| Agar | 8 g |

MS I Medium Stock

| Ingredient | Add per 1 L |
| --- | --- |
| $NH_4NO_3$ | 16.50 g |
| $KNO_3$ | 19 g |
| $CaCl_2—H_2O$ | 4.40 g |
| $MgSO_4—7H_2O$ | 3.70 g |
| $KH_2PO_4$ (monobasic) | 1.70 g |

Add one chemical at a time, in order, making sure it dissolves completely before adding the next.

MS II Medium Stock

| Ingredient | Add per 1 L |
| --- | --- |
| $H_3BO_3$ | 0.62 g |
| $MnSO_4\,H_2O$ (or $MnSO_4\,4H_2O$) | 1.69 g |

| Ingredient | Add per 1 L |
| --- | --- |
| (2.230 g) | |
| $ZnSO_4\,7H_2O$ | 0.86 g |
| KI | 0.083 g |
| $Na_2MoO_4\,2H_2O$ (or $H_2MoO_4\,2H_2O$) (or 0.0186 g) | 0.0250 g |
| $CuSo_4\,5H_2O$ (or $CuSo_4$) (or 0.0016 g) | 0.0025 g |
| $CoCl_2 6H_2O$ | 0.0025 g |

Add one chemical at a time, in order, making sure it dissolves completely before adding the next.

FeNaEDTA—Iron Stock

| Ingredient | Add per L |
| --- | --- |
| $Na_2EDTA$-$2H_2O$ (or $Na_2EDTA$) (or 33.5) | 37.24 g |
| $FeSO_4$—$7H_2O$ | 27.8 |

Mix together and stir over low heat until completely dissolved, autoclave, blow air through overnight, and store in an amber bottle at 4° C.

MB+ stock

| Ingredient | Add per 1 L |
| --- | --- |
| Glycine | 0.2 g |
| Thiamine-HCl | 0.01 g |
| Nicotinic acid | 0.05 g |
| Pyridoxine-HCl | 0.05 |
| Myo-Inositol | 10 g |

Bring up to volume and refrigerate

RMOP Medium Stock

| Ingredient | Add per 1 L |
| --- | --- |
| MS I | 100 ml |
| MS II | 10 ml |
| SB III | 10 ml |
| NaFeEDTA (0.1 M) | 1 ml |
| 6-BA (20 mg/l) | 50 ml |
| Casein hydrolysate | 0.5 g |
| NAA (100 mg/l) | 1 ml |
| Sucrose | 30 g |
| Bring up to volume and then pH | |
| pH | 5.21-5.8 |
| Add Gerlite | 2 g |

SB III (B5 Vitamin Stock)

| Ingredient | Add per 100 mL |
| --- | --- |
| Nicotinic acid | 10 mg |
| Thiamine HCL | 100 mg |
| Pyridoxine HCl | 10 mg |
| Myo-inositol | 1 g |

Add one chemical at a time, in order, making sure it dissolves completely before adding the next. Refrigerate.

| 6-BA (6-benzylaminopurine) 20 mg/l | Add per 1 L: 0.0200 g |
|---|---|

Add few drops of 1N KOH to 400 ml beaker. Dissolve the 6-BA in the KOH and add water. Be sure that the 6-BA is dissolved, rinse into 1 L volumetric flask and bring up to volume. Store in brown bottle in the refrigerator.

| NAA (naphthaleneacetic acid) 100 mg/l | Add per 1 L: 0.1 g |
|---|---|

1. Add 2 ml 95% ethanol to 400 ml beaker;
2. Add the powder;
3. Dissolve in Ethanol;
4. Meanwhile boil distilled water (100-200 mls) in a beaker;
5. Add boiling water to the beaker containing the ethanol and NAA;
6. The NAA should stay in solution;
7. Allow to cool;
8. Rinse carefully into a 1 L volumetric flask;
9. Bring up to volume. Refrigerate.

DOCUMENTS CITED

These documents are cited to the extent they relate to materials and methods, and are incorporated herein by reference.

Bernasconi et al., (1994) Functional expression of *Arabidopsis thaliana* anthranilate synthase subunit I in *Escherichia coli*. Plant Physiol 106: 353-358.

Cho et al., (2000) Increasing tryptophan synthesis in a forage legume *Astragalus sinicus* by expressing the tobacco feedback-insensitive anthranilate synthase (ASA2) gene. *Plant Physiol* 123: 1069-1076

Song et al., (1998) Tissue culture-specific expression of a naturally occurring tobacco feedback-insensitive anthranilate synthase. *Plant Physiol* 117: 533-543.

Svab et al., (1990) Stable transformation of plastids in higher plants. *Proc Natl Acad Sci USA* 87: 8526-8530.

Svab & Maliga P (1993) High-frequency plastid transformation in tobacco by selection for a chimeric aadA gene. *Proc Natl Acad Sci USA* 90: 913-917.

Widholm, (1981) Utilization of Indole Analogs by Carrot and Tobacco Cell Tryptophan Synthase in Vivo and in Vitro, Plant Physiol.; 67(6):1101-1104.

Zhang et al., (2001) Targeting a nuclear anthranilate synthase alpha-subunit gene to the tobacco plastid genome results in enhanced tryptophan biosynthesis. Return of a gene to its pre-endosymbiotic origin. *Plant Physiol.* 127(1): 131-41.

U.S. Pat. No. 6,388,174
U.S. Pat. No. 6,271,016
U.S. Pat. No. 6,118,047
U.S. Pat. No. 6,515,201

The invention claimed is:

1. A method of selecting a transformed plant cell, the method comprising:
   (a) expressing a nucleic acid sequence encoding a feedback insensitive anthranilate synthase (ASA2) in a plastid DNA (ptDNA); and
   (b) selecting the plant cell comprising a plastid that expresses the nucleic acid sequence by contacting the plant cell with a medium containing an indole analog, wherein the analog is at a concentration effective to inhibit the growth of a plant cell that does not express the nucleic acid sequence.

2. The method of claim 1, wherein the indole analog is selected from the group consisting of 4-fluoroindole, 5-fluoroindole, 6-fluoroindole, 6-aminoindole, 4-methylindole, 5 methoxyindole, 7-methoxyindole, and a combination thereof.

3. The method of claim 1, wherein the concentration of the indole analog ranges in concentration from 1 μM to about 10 mM.

4. A method for selecting a transformed plant cell, the method comprising:
   (a) expressing a nucleic acid sequence encoding a feedback insensitive anthranilate synthase (ASA2) or a functional fragment thereof in a plant cell by introducing the nucleic acid sequence in plastid DNA (ptDNA); and
   (b) selecting the plant cell that expresses the nucleic acid sequence by contacting the plant cell with a medium comprising indole analogs, at a concentration effective to inhibit the growth of a plant cell that does not express the nucleic acid sequence.

5. A homoplastomic plant regenereated from a plant cell, wherein the transformed plant cell comprises a nucleic acid sequence encoding a feedback insensitive anthranilate synthase (ASA2) in plastids or a functional fragment thereof as the sole selection marker.

6. The homoplastomic plant of claim 5 further comprising a gene of interest that confers one or more of the traits selected from the group consisting of disease resistance, increased biomass, reduced lignin content, increased nutritive value, stress tolerance, and pest resistance.

* * * * *